US011046758B2

(12) United States Patent
Prieur

(10) Patent No.: US 11,046,758 B2
(45) Date of Patent: Jun. 29, 2021

(54) COMBINATION THERAPY BETWEEN ANTI-PROGASTRIN ANTIBODY AND IMMUNOTHERAPY TO TREAT CANCER

(71) Applicant: Progastrine et Cancers S.À R.L., Luxembourg (LU)

(72) Inventor: Alexandre Prieur, Montpellier (FR)

(73) Assignee: PROGASTRINE ET CANCERS S.À R.L., Luxembourg (LU)

( * ) Notice: Subject to any disclaimer, the term of this patent is extended or adjusted under 35 U.S.C. 154(b) by 0 days.

(21) Appl. No.: 16/769,844

(22) PCT Filed: Dec. 5, 2018

(86) PCT No.: PCT/EP2018/083651
§ 371 (c)(1),
(2) Date: Jun. 4, 2020

(87) PCT Pub. No.: WO2019/110662
PCT Pub. Date: Jun. 13, 2019

(65) Prior Publication Data
US 2021/0009680 A1    Jan. 14, 2021

Related U.S. Application Data

(60) Provisional application No. 62/594,755, filed on Dec. 5, 2017.

(51) Int. Cl.
C07K 16/26 (2006.01)
C07K 16/28 (2006.01)
A61K 39/395 (2006.01)
A61P 35/00 (2006.01)

(52) U.S. Cl.
CPC .......... C07K 16/26 (2013.01); C07K 16/2818 (2013.01); C07K 2317/24 (2013.01); C07K 2317/565 (2013.01); C07K 2317/76 (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,716,111 A | 12/1987 | Osband et al. |
| 4,975,278 A | 12/1990 | Senter et al. |
| 5,219,996 A | 6/1993 | Bodmer et al. |
| 5,530,101 A | 6/1996 | Queen et al. |
| 5,546,806 A | 8/1996 | Kain |
| 5,565,332 A | 10/1996 | Hoogenboom et al. |
| 5,585,089 A | 12/1996 | Queen et al. |
| 5,639,641 A | 6/1997 | Pedersen et al. |
| 5,693,761 A | 12/1997 | Queen et al. |
| 5,792,632 A | 8/1998 | Dujon et al. |
| 5,814,318 A | 9/1998 | Lonberg et al. |
| 5,830,729 A | 11/1998 | Jaisser et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 6,238,924 B1 | 5/2001 | Dujon et al. |
| 9,611,320 B2* | 4/2017 | Pannequin ................. A61P 1/00 |
| 9,683,048 B2* | 6/2017 | Freeman ................. A61P 43/00 |
| 2019/0002582 A1* | 1/2019 | Prieur .............. G01N 33/57449 |
| 2019/0011447 A1* | 1/2019 | Prieur ...................... A61P 35/00 |
| 2019/0011449 A1* | 1/2019 | Prieur ................... G01N 33/577 |
| 2020/0103410 A1* | 4/2020 | Prieur .............. G01N 33/57423 |
| 2020/0200751 A1* | 6/2020 | Prieur ..................... C07K 16/28 |

FOREIGN PATENT DOCUMENTS

| | | |
|---|---|---|
| EP | 0451261 B1 | 10/1991 |
| EP | 0519596 A1 | 12/1992 |
| EP | 0566647 B1 | 10/1993 |
| EP | 0592106 A1 | 4/1994 |
| EP | 0682040 A1 | 11/1995 |
| EP | 0939127 A2 | 9/1999 |
| EP | 0948544 B1 | 10/1999 |
| EP | 1391213 A1 | 2/2004 |
| EP | 17305381.0 | * 3/2017 |
| EP | 17305382.8 | * 3/2017 |
| WO | 9110741 A1 | 7/1991 |
| WO | 9321232 A1 | 10/1993 |
| WO | 9411026 A2 | 5/1994 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |

(Continued)

OTHER PUBLICATIONS

Giraud et al. (2016) Autocrine Secretion of Progastrin Promotes the Survival and Self-Renewal of Colon Cancer Stem-like Cells. Cancer Res; 76(12); 3618-3628.*

Fessas et al., *A molecular and preclinical comparison of the PD-1-targeted T-cell checkpoint inhibitors nivolumab and pembrolizumab*, 44 Seminars in Oncology 136-140 (2017).

Katoh, *Canonical and non-canonical WNT signaling in cancer stem cells and their niches: Cellular heterogeneity, omics reprogramming, targeted therapy and tumor plasticity (Review)*, 51 International Journal of Oncology 1357-1369 (2017).

Prieur et al., *Targeting the Wnt Pathway and Cancer Stem Cells with Anti-progastrin Humanized Antibodies as a Potential Treatment for K-RAS-Mutated Colorectal Cancer*, 23(17) Clin Cancer Res 5267-5280 (Sep. 1, 2017).

(Continued)

*Primary Examiner* — Ilia I Ouspenski
(74) *Attorney, Agent, or Firm* — Panitch Schwarze Belisario & Nadel LLP

(57) ABSTRACT

The present invention relates to combinations comprising anti-progastrin (anti-hPG) monoclonal antibodies and immune checkpoint inhibitors, as well as pharmaceutical compositions comprising said combinations. Methods of treatment of cancer using said combinations are also provided.

Figure 1:
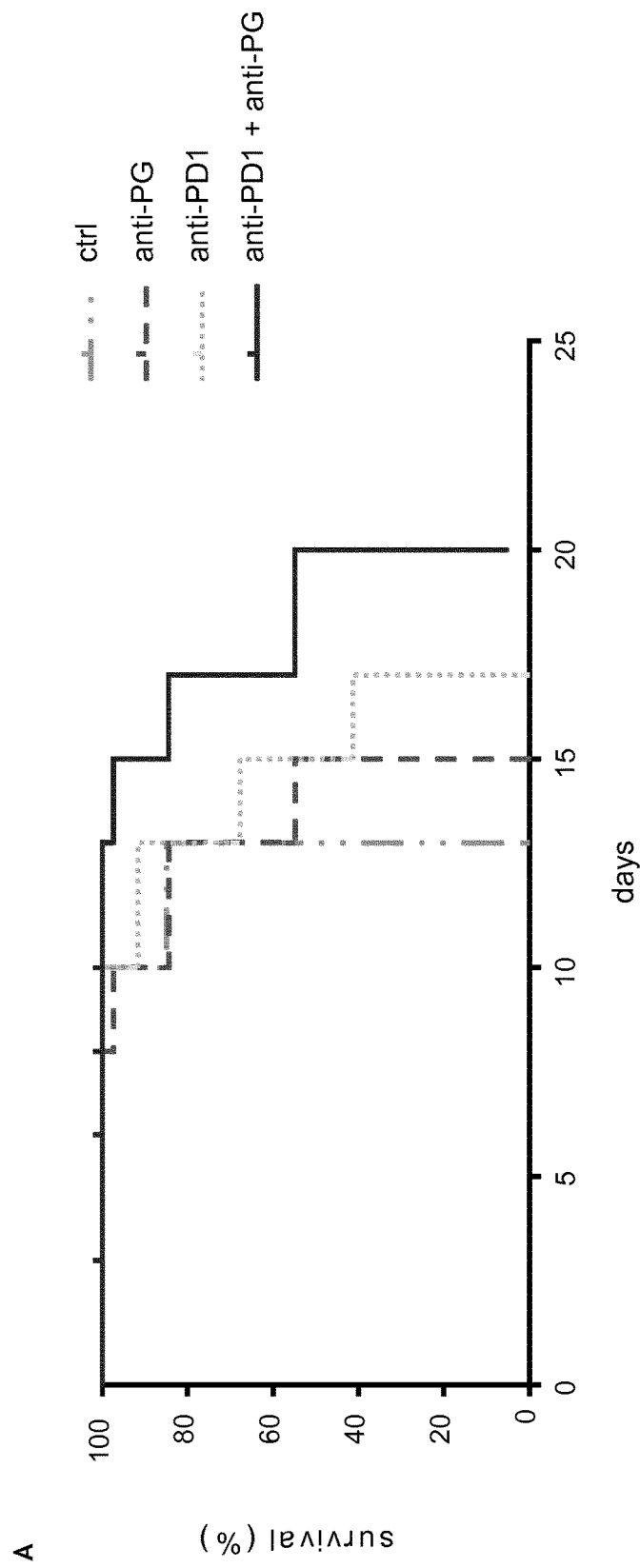

18 Claims, 2 Drawing Sheets
Specification includes a Sequence Listing.

(56) References Cited

FOREIGN PATENT DOCUMENTS

| WO | 03025183 A2 | 3/2003 |
| WO | 2004067753 A2 | 8/2004 |
| WO | 2009054985 A1 | 4/2009 |
| WO | 2011083088 A2 | 7/2011 |
| WO | 2017114976 A1 | 7/2017 |
| WO | WO 2017/114976 | 7/2017 |

OTHER PUBLICATIONS

Sanborn et al., *Abstract CT023: Phase I results from the combination of an immune-activating anti-CD27 antibody (varlilumab) in combination with PD-1 blockade (nivolumab): activation across multiple Immune pathways without untoward immune-related adverse events*, 78(14) Cancer Research 1-2 (Jul. 2016).

Sawada et al., *Programmed death-1 blockade enhances the antitumor effects of peptide vaccine-induced peptide-specific cytotoxic T lymphocytes*, 46 International Journal of Oncology 28-36 (2015).

Tsukihara et al., *Efficacy of trifluridine/tipiracil + anti-mouse PD-1 antibody combination on mouse colorectal cancer model*, J-3080 109(Supp. 1) The 76$^{th}$ Annual Meeting of the Japanese Cancer Association 847 (Sep. 28, 2017).

Notification of Transmittal of The International Preliminary Report on Patentability Report issued in PCT/EP2018/083651 dated Oct. 30, 2019 (PCT/IPEA/416—1 Page).

International Preliminary Report on Patentability Report issued in PCT/EP2018/083651 dated Oct. 30, 2019 (PCT/IPEA/409—16 Pages).

Notification of Transmittal of The International Search Report and The Written Opinion of the International Searching Authority, or the Declaration, issued in PCT/EP2018/083651 dated Mar. 14, 2019 (PCT/ISA/220—1 Page).

International Search Report issued in PCT/EP2018/083651 dated Mar. 14, 2019 (6 Pages) (PCT/ISA/210—6 Pages).

Written Opinion of the International Searching Authority issued in PCT/EP2018/083651 dated Mar. 14, 2019 (PCT/ISA/237—9 Pages).

Birch et al., Antibody production, 58 Advanced Drug Delivery Reviews 671-685 (2006).

Chau et al., Treatment in advanced colorectal cancer: what, when and how?, 100 British Journal of Cancer 1704-1719 (2009).

Cockett et al., High Level Expression of Tissue Inhibitor of Metalloproteinases in Chinese Hamster Ovary Cells Using Glutamine Synthetase Gene Amplification 8 Bio/Technology, 662-667 (Jul. 1990).

Crouse et al., Expression and Amplification of Engineered Mouse Dihydrofolate Reductase Minigenes, 3(2) Molecular and Cellular Biology 257-266 (Feb. 1983).

Field et al., Metastatic colorectal cancer-past, progress and future 13(28) World Journal of Gastroenterology, 3806-3815 (Jul. 2007).

Foecking et al., Powerful and versatile enhancer-promoter unit for mammalian expression vectors, 45 Gene 101-105 (1986).

Hinman et al., Preparation and Characterization of Monoclonal Antibody Conjugates of the Calicheamicins: A Novel and Potent Family of Antitumor Antibiotics, 53 Cancer Research 3336-3342 (Jul. 1993).

Huston et al., Protein engineering of antibody binding sites: Recovery of specific activity in an anti-digoxin single-chain Fv analogue produced in *Escherichia coli*, 85 Proc. Natl. Acad. Sci. USA 5879-5883 (Aug. 1988).

Jones et al. Replacing the complementarity-determining regions in a human antibody with those from a mouse, 321 Nature 522-525 (May 1986).

Kaas et al., IMGT Colliers de Perles: Standardized Sequence-Structure Representations of the IgSF and MhcSF Superfamily Domains, 2 Current Bioinformatics 21-30 (2007).

Kaas et al., IMGT/3Dstructure-DB and IMGT/StructuralQuery, a database and a tool for immunoglobulin, T cell receptor and MHC structural data, 32 Nucleic Acids Research D208-D210 (2004).

Kam et al., Carbon nanotubes as multifunctional biological transporters and near-infrared agents for selective cancer cell destruction 102(33) PNAS 11600-11605 (Aug. 2005).

Kavecansky et al., Beyond Checkpoint Inhibitors: The Next Generation of Immunotherapy in Oncology, 13(2) The American Journal of Hematology/ Oncology 9-20 (2017).

Lefranc et al., IMGT unique numbering for immunoglobulin and T cell receptor variable domains and Ig superfamily V-like domains, 27 Developmental and Comparative Immunology 55-77 (2003).

Lefranc, The IMGT Unique Numbering for Immunoglobulins, T-Cell Receptors, and Ig-Like Domains, 7(4) The Immunologist 132-136 (1999).

Lefranc, Unique database numbering system for immunogentic analysis, 18(11) Immunogenetics 509 (Nov. 1997).

Liu et al., Eradication of large colon tumor xenografts by targeted delivery of maytansinoids 93 Proc. Natl. Acad. Sci. 8618-8623 (Aug. 1996).

Lode et al., Targeted Therapy with a Novel Enediyene Antibiotic Calicheamicin Ø Effectively Suppresses Growth and Dissemination of Liver Metastases in a Syngeneic Model of Murine Neuroblastoma, 58 Cancer Research 2925-2928 (Jul. 1998).

Lowy et al., Isolation of Transforming DNA: Cloning the Hamster aprt Gene, 22 Cell 817-823 (Dec. 1980).

Mandler et al., Immunoconjugates of Geldanamycin and Anti-HER2 Monoclonal Antibodies: Antiproliferative Activity on Human Breast Carcinoma Cell Lines, 92(19) Journal of National Cancer Institute 1573-1581 (Oct. 2000).

Mandler et al., Synthesis and Evaluation of Antiproliferative Activity of a Geldanamycin-Herceptin Immunoconjugate, 10 Bioorganic & Medicinal Chemistry Letters 1025-1028 (2000).

Martin-Acevedo et al., Next generation of immune checkpoint therapy in cancer: new developments and challenges, 11(39) Journal of Hematology & Oncology 20 pages (2018).

Moehle et al., Targeted gene addition into a specified location in the human genome using designed zinc finger nucleases, 104(9) PNAS 3055-3060 (Feb. 2007).

Mulligan et al., Selection for animal cells that express the *Escherichia coli* gene coding for xanthine-guanine phosphorisbosyltransferase, 78(4) Proc. Natl. Acad. Sci. USA 2072-2076 (Apr. 1981).

Padlan, A Possible Procedure for Reducing the Immunogenicity of Antibody Variable Domains While Preserving their Ligand-Binding Properties 28(4/5) Molecular Immunology 489-498 (1991).

Payne, Progress in immunoconjugate cancer therapeutics, 3 Cancer Cell 207-212 (Mar. 2003).

Prieur et al., Targeting the Wnt Pathway and Cancer Stem Cells with Anti-progastrin Humanized Antibodies as a Potential Treatment for K-RAS-Mutated Colorectal Cancer, 23(17) Clinical Cancer Research 5267-5280 (Jun. 2017).

Reik et al., Enhanced Protein Production by Engineered Zinc Finger Proteins, 97(5) Biotechnology and Bioengineering 1180-1189 (Aug. 2007).

Roguska et al., Humanization of murine monoclonal antibodies through variable domain resurfacing, 91 Proc. Natl. Acad. Sci. USA 969-973 (Feb. 1994).

Ruiz et al., IMGT gene identification and Colliers de Perles of human immunogloublins with known 3D structures, 53 Immunogenetics 857-883 (2002).

Sanborn etal., Abstract CT023: Phase I results from the combination of an immune-activating anti-CD27 antibody (varlilumab) in combination with PD-1 blockade (nivolumab): activation across multiple immune pathways without untoward immune-related adverse events, 76(14) Cancer Research (Jul. 2016) (Abstract Only).

Santerre et al., Expression of prokaryotic genes for hygromycin B and G418 resistance as dominant-selection markers in mouse L cells, 30 Gene 147-156 (1984).

Singer et al., Optimal Humanization of 1B4, an Anti-CD18 Murine Monoclonal Antibody, is Achieved by Correct Choice of Human V-Region Framework Sequences, 150(7) The Journal of Immunology 2844-2857 (Apr. 1993).

Studnicka et al., Human-engineered monoclonal antibodies retain full specific binding activity by preserving non-CDR complentarity-modulating residues, 7(6) Protein Engineering 805-814 (1994).

(56) References Cited

OTHER PUBLICATIONS

Tsukihara et al., Efficacy of trifluridine/tipiracil + anti-mouse PD-1 antibody combination on mouse colorectal cancer model, 109(1) 76th Annual Meeting of the Japanese Cancer Association 1 page (2017).
Vitetta et al., Redesigning Nature's Poisons to Create Anti-Tumor Reagents, 238 Science 1098-1104 (Nov. 1987).
Wei et al., Fundamental Mechanisms of Immune Checkpoint Blockade Therapy, Cancer Discovery 1069-1086 (Aug. 2018).
Wigler et al., Transfer of Purified Herpes Virus Thymidine Kinase Gene to Cultured Mouse Cells, 11 Cell 223-232 (May 1977).
Wigler et al., Transformation of mammalian cells with an amplifiable dominant-acting gene, 77(6) Proc. Natl. Acad. Sci. USA 3567-3570 (Jun. 1980).
Wu et al., Delivery systems for gene therapy, 3 Biotherapy 87-95 (1991).

* cited by examiner

COMBINATION THERAPY BETWEEN ANTI-PROGASTRIN ANTIBODY AND IMMUNOTHERAPY TO TREAT CANCER

CROSS-REFERENCE TO RELATED APPLICATIONS

This application is a U.S. National Stage Application pursuant to 35 U.S.C. § 371 of International Patent Application PCT/EP2018/083651, filed on Dec. 5, 2018, and published as WO 2019/110662 on Jun. 13, 2019, which claims priority to U.S. Patent Application No. 62/594,755, filed on Dec. 5, 2017, all of which are incorporated herein by reference in their entireties for all purposes.

INTRODUCTION

Immunotherapy has been a game-changer in the field of cancer therapy. Human cancers carry a multitude of somatic gene mutations and epigenetically altered genes, the products of which are potentially recognizable as foreign antigens. Tumour cells escape the endogenous immune response by inducing tolerance among tumour-specific T cells. In order to ensure that an immune inflammatory response is not constantly activated once tumour antigens have stimulated a response, multiple controls or "checkpoints" are in place or activated. These immune checkpoints are mostly represented by T-cell receptor binding to ligands on cells in the surrounding tumour microenvironment, forming immunological synapses which then regulate the function of the T cell.

One approach to trigger antitumour immune responses has been termed "checkpoint blockade", referring to the blockade of immune-inhibitory pathways activated by cancer cells. Developments in immune checkpoint-based therapy are progressing at a breath-taking pace. A major turning point has been crossed with the arrival of new molecules acting on the immune system (defense system of an organism vis-á-vis of a pathogen) and effective in certain cancers. Use of these news molecules allowed to observe tumour regression in some patients with cutaneous melanoma. Recent approvals of several blockers of the cytotoxic T lymphocyte (CTL)-associated antigen-4—CD80/CD86 pathway (Ipilimumab/Yervoy) and the PD-1—PD-L1/PD-L2 pathway, such as nivolumab (Opdivo), pembrolizumab (Keytruda), or atezolizumab (Tecentriq), ushered immune checkpoint (IC) inhibitors (ICIs) as the key component of advanced cancer treatment.

However, even in melanoma, most patients show only limited or transient response, while such common cancers as breast, prostate, or colon cancer respond only sporadically. In addition, pancreatic and colorectal adenocarcinomas remain by and large resistant to these treatment modalities, specifically single agent PD-1 blockade. Despite observations of durable responses to checkpoint-blocking antibodies, it is thus clear that not all patients even within the subsets of immunotherapy-responsive cancers demonstrate tumour regression.

Therefore, there is still a need to identify additional pathways that provide either agonism or additional inhibition to existing immune checkpoint inhibitors pathways.

Description

The present inventors have shown that the combination of a molecule binding to progastrin and an immune checkpoint inhibitor results in greater therapeutic efficacy against cancer. Notably, the inventors showed that administering an anti-progastrin monoclonal antibody in combination with an immune checkpoint inhibitor such as an anti-PD-1 antibody significantly increases the survival of colorectal cancer cell lines xenografted mice. This is illustrated by a median survival time which is significantly increased compared to each of the therapies alone. Moreover, the combination of said anti-progastrin monoclonal antibody and immune checkpoint inhibitor leads to a level of expression of interferon γ which is more than doubled.

In a first aspect, the present invention relates to a combination comprising a progastrin-binding molecule and an immune checkpoint inhibitor. Preferably, the invention relates to a combination of a progastrin-binding molecule and an immune checkpoint inhibitor.

Immune Checkpoint Inhibitors

As used herein, a "checkpoint inhibitor" refers to a molecule, such as e.g., a small molecule, a soluble receptor, or an antibody, which targets an immune checkpoint and blocks the function of said immune checkpoint. More specifically, a "checkpoint inhibitor" as used herein is a molecule, such as e.g., a small molecule, a soluble receptor, or an antibody, that blocks certain proteins made by some types of immune system cells, such as T cells, and some cancer cells. Such proteins, the "immune checkpoints" or "immune checkpoint proteins" as used herein, regulate T cell function in the immune system. Notably, they help keep immune responses in check and can keep T cells from killing cancer cells. Said immune checkpoint proteins achieve this result by interacting with specific ligands which send a signal into the T cell and essentially switch off or inhibit T cell function. Inhibition of these proteins results in restoration of T cell function and an immune response to the cancer cells. Examples of checkpoint proteins include, but are not limited to CTLA-4, PDL1, PDL2, PD1, B7-H3, B7-H4, BTLA, HVEM, TIM3, GAL9, LAG3, VISTA, KIR, 264 (belongs to the CD2 family of molecules and is expressed on all NK, γδ, and memory CD8+ (αβ) T cells), CD 160 (also referred to as BY55), CGEN-15049, CHK 1 and CHK2 kinases, IDO1, A2aR and various B-7 family ligands.

In a first embodiment, the immune checkpoint inhibitor is an inhibitor of any one of CTLA-4, PDL1, PDL2, PD1, B7-H3, B7-H4, BTLA, HVEM, TIM3, GAL9, LAG3, VISTA, KIR, 264 (belongs to the CD2 family of molecules and is expressed on all NK, γδ, and memory CD8+ (αβ) T cells), CD 160 (also referred to as BY55), CGEN-15049, CHK 1 and CHK2 kinases, IDO1, A2aR and any of the various B-7 family ligands.

As used herein, an "inhibitor" or "antagonist" refers to a molecule that is capable of inhibiting or otherwise decreasing one or more of the biological activities of a target protein, such as any one of the immune checkpoint proteins described above. In some embodiments, an inhibitor of an immune checkpoint protein (e.g., an antagonistic antibody provided herein) can, for example, act by inhibiting or otherwise decreasing the activation and/or cell signalling pathways of the cell expressing said immune checkpoint protein (e.g., a T cell), thereby inhibiting a biological activity of the cell relative to the biological activity in the absence of the antagonist.

Exemplary immune checkpoint inhibitors include anti-CTLA-4 antibody (e.g., ipilimumab), anti-LAG-3 antibody (e.g., BMS-986016), anti-B7-H3 antibody, anti-B7-H4 antibody, anti-Tim3 antibody (e.g., TSR-022, MBG453), anti-BTLA antibody, anti-KIR antibody, anti-A2aR antibody, anti CD200 antibody, anti-PD-1 antibody (e.g., pembrolizumab, nivolumab, cemiplimab, pidilizumab), anti-PD-L1 antibody (e.g., atezolizumab, avelumab, durvalumab, BMS 936559), anti-VISTA antibody (e.g., JNJ 61610588), anti- CD28 antibody, anti-CD80 or -CD86 antibody, anti-B7RP1 antibody, anti-B7-H3 antibody, anti-HVEM antibody, anti-CD137 antibody (e.g., urelumab), anti-CD137L antibody, anti-OX40 (e.g., 9612, PF-04518600, MED16469), anti-OX40L antibody, anti-CD40 or -CD40L antibody, anti-GAL9 antibody, anti-IL-10 antibody, fusion protein of the extracellular domain of a PD-1 ligand, e.g. PDL-1 or PD-L2, and IgG1 (e.g., AMP-224), fusion protein of the extracellular domain of a OX40 ligand, e.g. OX40L, and IgG1 (e.g., MED16383), IDO1 drug (e.g., epacadostat) and A2aR drug. A number of immune checkpoint inhibitors have been approved or are currently in clinical trials. Such inhibitors include ipilimumab, pembrolizumab, nivolumab, cemiplimab, pidilizumab, atezolizumab, avelumab, durvalumab, BMS 936559, JNJ 61610588, urelumab, 9612, PF-04518600, BMS-986016, TSR-022, MBG453, MED16469, MED16383, and epacadostat.

Examples of immune checkpoints inhibitors are listed for example in Marin-Acevedo et al., *Journal of Hematology & Oncology* 11: 8, 2018; Kavecansky and Pavlick, *AJHO* 13(2): 9-20, 2017; Wei et al., *Cancer Discov* 8(9): 1069-86, 2018.

Preferably, the immune checkpoint inhibitor is an inhibitor of CTLA-4, LAG-3, Tim3, PD-1, PD-L1, VISTA, CD137, OX40, or IDO1.

In some embodiment, the inhibitor is a small molecule drug. In some embodiment, the inhibitor is a soluble receptor. In some embodiments, the inhibitor is an antibody.

A "small molecule drug" is broadly used herein to refer to an organic, inorganic, or organometallic compound typically having a molecular weight of less than about 1000. Small molecule drugs of the invention encompass oligopeptides and other biomolecules having a molecular weight of less than about 1000.

By "soluble receptor", it is herein referred to a peptide or a polypeptide comprising the extracellular domain of a receptor, but not the transmembrane or the cytoplasmic domains thereof.

The term "antibody" as used herein is intended to include polyclonal and monoclonal antibodies. An antibody (or "immunoglobulin") consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Method for identifying the CDRs within light and heavy chains of an antibody and determining their sequence are well known to the skilled person. For the avoidance of doubt, in the absence of any indication in the text to the contrary, the expression CDRs means the hypervariable regions of the heavy and light chains of an antibody as defined by IMGT, wherein the IMGT unique numbering provides a standardized delimitation of the framework regions and of the complementary determining regions, CDR1-IMGT: 27 to 38, CDR2.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. Antibodies can be of different isotypes (namely IgA, IgD, IgE, IgG or IgM).

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunised animal.

The term "monoclonal antibody" designates an antibody arising from a nearly homogeneous antibody population, wherein population comprises identical antibodies except for a few possible naturally-occurring mutations which can be found in minimal proportions. A monoclonal antibody arises from the growth of a single cell clone, such as a hybridoma, and is characterized by heavy chains of one class and subclass, and light chains of one type.

In some embodiment, the inhibitor is an antagonistic antibody, i.e. an antibody that inhibits or reduces one or more of the biological activities of an antigen, such as any one of the immune checkpoint proteins described herein. Certain antagonistic antibodies substantially or completely inhibit one or more of the biological activities of said antigen. The term "inhibit," or a grammatical equivalent thereof, when used in the context of an antibody refers to an antibody that suppresses, restrains or decreases a biological activity of the antigen to which the antibody binds. The inhibitory effect of an antibody can be one which results in a measurable change in the antigen's biological activity.

In an embodiment, the immune checkpoint inhibitor is selected in the group consisting of ipilimumab, pembrolizumab, nivolumab, cemiplimab, pidilizumab, atezolizumab, avelumab, durvalumab, BMS 936559, JNJ 61610588, urelumab, 9612, PF-04518600, BMS-986016, TSR-022, MBG453, MEDI6469, MEDI16383, and epacadostat.

In an embodiment, the immune checkpoint inhibitor is an inhibitor of CTLA-4, PD-1, or PD-L1. In a preferred embodiment, said immune checkpoint inhibitor is an antibody against any one of CTLA-4, PD-1, or PD-L1. More preferably, said antibody is an antagonist antibody. Even more preferably, said antagonist antibody is selected between ipilimumab, pembrolizumab, nivolumab, cemiplimab, pidilizumab, atezolizumab, avelumab, and durvalumab.

In an embodiment, the immune checkpoint inhibitor is an inhibitor of PD-1. In a preferred embodiment, said immune checkpoint inhibitor is an antibody against PD-1. More preferably, said antibody is an antagonist antibody. Even more preferably, the immune checkpoint inhibitor is pembrolizumab, nivolumab, cemiplimab, or pidilizumab.

Anti-hPG Antibodies

Progastrin (PG) is produced by colorectal tumour cells and is thought to stimulate proliferation of these cells by triggering a signal transduction pathway that blocks the cells' normal differentiation processes, including those processes that lead to cell death. Depletion of the gastrin gene transcript that encodes progastrin induces cell differentiation and programmed cell death in tumour cells in in vitro and in vivo CRC models, reducing tumour cell proliferation. While not intending to be bound by any theory of operation, through binding of PG, anti-hPG antibodies are thought to block or inhibit its ability to interact with its signalling partner(s). This, in turn, inhibits a signal transduction pathway in colorectal tumour cells that would otherwise lead to proliferation.

Human pre-progastrin, a 101 amino acids peptide (Amino acid sequence reference: AAB19304.1), is the primary translation product of the gastrin gene. Progastrin (PG) is formed by cleavage of the first 21 amino acids (the signal peptide) from preprogastrin. The 80 amino-acid chain of progastrin is further processed by cleavage and modifying enzymes to several biologically active gastrin hormone forms: gastrin 34 (G34) and glycine-extended gastrin 34 (G34-Gly), comprising amino acids 38-71 of progastrin, gastrin 17 (G17) and glycine-extended gastrin 17 (G17-Gly), comprising amino acids 55 to 71 of progastrin.

The term "progastrin" designates the mammalian progastrin peptide, and particularly human progastrin. For the avoidance of doubt, without any specification, the expression "human progastrin" or "hPG" refers to human PG of sequence SEQ ID No. 1. Human progastrin comprises notably a N-terminus domain and a C-terminus domain which are not present in the biologically active gastrin hormone forms mentioned above. Preferably, the sequence of said N-terminus domain is represented by SEQ ID NO. 2. In another preferred embodiment, the sequence of said C-terminus domain is represented by SEQ ID NO. 3.

By "progastrin-binding molecule", it is herein referred to any molecule that binds progastrin, but does not bind gastrin-17 (G17), gastrin-34 (G34), glycine-extended gastrin-17 (G17-Gly), or glycine-extended gastrin-34 (G34-Gly) and C-terminal flanking peptide (CTFP). The progastrin-binding molecule of the present invention may be any progastrin-binding molecule, such as, for instance, an antibody molecule or a receptor molecule. Preferably, the progastrin-binding molecule is an anti-progastrin antibody (an anti-hPG antibody) or an antigen-binding fragment thereof.

By "binding", "binds", or the like, it is meant that the antibody, or antigen binding fragment thereof, forms a complex with an antigen which, under physiologic conditions, is relatively stable. Methods for determining whether two molecules bind are well known in the art and include, for example, equilibrium dialysis, surface plasmon resonance, and the like. In a particular embodiment, said antibody, or antigen-binding fragment thereof, binds to progastrin with an affinity that is at least two-fold greater than its affinity for binding to a non-specific molecule such as BSA or casein. In a more particular embodiment, said antibody, or antigen-binding fragment thereof, binds only to progastrin.

In a more specific embodiment, the present anti-hPG antibody recognizes an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID N° 1.

In a more specific embodiment, the anti-hPG antibody recognizes an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID N° 40), residues 76 to 80 of hPG, or residues 67 to 74 of hPG, wherein the amino acid sequence of hPG is SEQ ID N° 1.

In a more particular embodiment, the anti-hPG antibody has an affinity for progastrin of at least 5000 nM, at least 500 nM, 100 nM, 80 nM, 60 nM, 50 nM, 40 nM, 30 nM, 20 nM, 10 nM, 7 nM, 5 nM, 4 nM, 3 nM, 2 nM, 1 nM, 0.5 nM, 0.1 nM, 50 pM, 10 pM, 5 pM, 1 pM, or at least 0.1 pM, as determined by a method such described herein.

Preferably, the anti-hPG antibody is a neutralising anti-hPG antibody.

The expression "neutralising anti-hPG antibody" designates an antibody that binds PG and blocks PG-dependent signalling, resulting in the inhibition of PG-induced responses in tumour cells, and particularly in CRC tumour cells. Inhibiting PG-induced responses of cancer cells may be mediated by repression of cell differentiation, repression of cell death, and/or stimulation of cell proliferation.

In a particular embodiment, said progastrin-binding antibody, or an antigen-binding fragment thereof, is selected from the group consisting of: polyclonal antibodies, monoclonal antibodies, chimeric antibodies, single chain antibodies, camelised antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

In another particular embodiment, the antibody binding to progastrin has been obtained by an immunisation method known by a person skilled in the art, wherein using as an immunogen a peptide which amino acid sequence comprises the totality or a part of the amino-acid sequence of progastrin. More particularly, said immunogen comprises a peptide chosen among:

a peptide which amino acid sequence comprises, or consists of, the amino acid sequence of full length progastrin, and particularly full length human progastrin of SEQ ID N° 1, a peptide which amino acid sequence corresponds to a part of the amino acid sequence of progastrin, and particularly full length human progastrin of SEQ ID N° 1, a peptide which amino acid sequence corresponds to a part or to the whole amino acid sequence of the N-terminal part of progastrin, and in particular peptides comprising, or consisting of, the amino acid sequence: SWKPRSQQPDAPLG (SEQ ID N° 2), and a peptide which amino acid sequence corresponds to a part or to the whole amino acid sequence of the C-terminal part of progastrin, and in particular peptides comprising, or consisting of, the amino acid sequence: QGPWLEEEEEAYGWMDFGRRSAEDEN (SEQ ID N° 3), a peptide which amino acid sequence corresponds to a part of the amino acid sequence of the C-terminal part of progastrin, and in particular peptides comprising the amino acid sequence FGRRSAEDEN (SEQ ID N° 40) corresponding to amino acids 71-80 of progastrin The skilled person will realize that such immunisation may be used to generate either polyclonal or monoclonal antibodies, as desired. Methods for obtaining each of these types of antibodies are well known in the art. The skilled person will thus easily select and implement a method for generating polyclonal and/or monoclonal antibodies against any given antigen.

Examples of monoclonal antibodies which were generated by using an immunogen comprising the amino-acid sequence "SWKPRSQQPDAPLG", corresponding to the amino acid sequence 1-14 of human progastrin (N-terminal extremity) include, but are not restricted to, monoclonal antibodies designated as: mAb3, mAb4, mAb16, and mAb19 and mAb20, as described in the following Table 1 to Table 4. Other monoclonal antibodies have been described, although it is not clear whether these antibodies actually bind progastrin (WO 2006/032980). Experimental results of epitope mapping show that mAb3, mAb4, mAb16, and mAb19 and mAb20 do specifically bind an epitope within said hPG N-terminal amino acid sequence. Polyclonal antibodies recognizing specifically an epitope within the N-terminus of progastrin represented by SEQ ID NO. 2, have been described in the art (see e.g., WO 2011/083088).

TABLE 1

| Hybridoma deposit | mAb | Amino acid sequences | | SEQ ID No |
|---|---|---|---|---|
| 61351311C10 | mAb3 | VH CDR 1 | GYIFTSYW | SEQ ID No 4 |
| | | VH CDR 2 | FYPGNSDS | SEQ ID No 5 |
| | | VH CDR 3 | TRRDSPQY | SEQ ID No 6 |
| | | VL CDR 1 | QSIVHSNGNTY | SEQ ID No 7 |
| | | VL CDR 2 | KVS | SEQ ID No 8 |
| | | VL CDR 3 | FQGSHVPFT | SEQ ID No 9 |
| | | mVH 3 | EVQLQQSGTVLARPGASVKMSCK ASGYIFTSYWVHWVKQRPGQGLE WIGGFYPGNSDSRYNQKFKGKAT LTAVTSASTAYMDLSSLTNEDSA VYFCTRRDSPQYWGQGTTLTVSS | SEQ ID No 41 |
| | | mVL 3 | DVLMTQTPLSLPVSLGDQASISC RSSQSIVHSNGNTYLEWYLQKPG QSPKLLIYKVSNRFSGVPDRFSG SGSGTDFTLKISRLEAEDLGVYY CFQGSHVPFTFGGGTKLEIK | SEQ ID No 42 |
| | | huVH 3 | QVQLVQSGAEVKKPGASVKVSCK ASGYIFTSYWVHWVRQAPGQRLE WMGGFYPGNSDSRYSQKFQGRVT ITRDTSASTAYMELSSLRSEDTA VYYCTRRDSPQYWGQGTLVTVSS | SEQ ID No 53 |
| | | huVL 3 | DVVMTQSPLSLPVTLGQPASISC RSSQSIVHSNGNTYLEWFQQRPG QSPRRLIYKVSNRFSGVPDRFSG SGSGTDFTLKISRVEAEDVGVYY CFQGSHVPFTFGGGTKVEIK | SEQ ID No 54 |

TABLE 2

| Hybridoma deposit | mAb | Amino acid sequences | | SEQ ID No |
|---|---|---|---|---|
| 20D2C3G2 | mAb4 | VH CDR 1 | GYTFSSW | SEQ ID No 10 |
| | | VH CDR 2 | FLPGSGST | SEQ ID No 11 |
| | | VH CDR 3 | ATDGNYDWFAY | SEQ ID No 12 |
| | | VL CDR 1 | QSLVHSSGVTY | SEQ ID No 13 |

TABLE 2-continued

| Hybridoma deposit | mAb | Amino acid sequences | | SEQ ID No |
|---|---|---|---|---|
| | | VL CDR 2 | KVS | SEQ ID No 14 |
| | | VL CDR 3 | SQSTHVPPT | SEQ ID No 15 |
| | | mVH 4 | QVQLQQSGAELMKPGASVKISCK ATGYTFSSSWIEWLKQRPGHGLE WIGEFLPGSGSTDYNEKFKGKAT FTADTSSDTAYMLLSSLTSEDSA VYYCATDGNYDWFAYWGQGTLVT VSA | SEQ ID No 43 |
| | | mVL 4 | DLVMTQTPLSLPVSLGDQASISC RSSQSLVHSSGVTYLHWYLQKPG QSPKLLIYKVSNRFSGVPDRFSG SGSGTDFTLKISRVEAEDLGVYF CSQSTHVPPTFGSGTKLEIK | SEQ ID No 44 |
| | | huVH 4 | QVQLVQSGAEVKKPGASVKVSCK ASGYTFSSSWMHWVRQAPGQGLE WMGIFLPGSGSTDYAQKFQGRVT MTRDTSTSTVYMELSSLRSEDTA VYYCATDGNYDWFAYWGQGTLVT VSS | SEQ ID No 55 |
| | | huVL 4 | DIVMTQTPLSLSVTPGQPASISC KSSQSLVHSSGVTYLYWYLQKPG QSPQLLIYKVSNRFSGVPDRFSG SGSGTDFTLKISRVEAEDVGVYY CSQSTHVPPTFGQGTKLEIK | SEQ ID No 56 |

TABLE 3

| Hybridoma deposit | mAb | Amino acid sequences | | SEQ ID No |
|---|---|---|---|---|
| 1E9D9B6 | mAb16 | VH CDR 1 | GYTFTSYY | SEQ ID No 16 |
| | | VH CDR 2 | INPSNGGT | SEQ ID No 17 |
| | | VH CDR 3 | TRGGYYPFDY | SEQ ID No 18 |
| | | VL CDR 1 | QSLLDSDGKTY | SEQ ID No 19 |
| | | VL CDR 2 | LVS | SEQ ID No 20 |
| | | VL CDR 3 | WQGTHSPYT | SEQ ID No 21 |
| | | mVH 16 | QVQLQQSGAELVKPGASVKLSCK ASGYTFTSYYMYWVKQRPGQGLE WIGEINPSNGGTNFNEKFKSKAT LTVDKSSSTAYMQLSSLTSEDSA VYYCTRGGYYPFDYWGQGTTLTV SS | SEQ ID No 45 |
| | | mVL 16 | DVVMTQTPLTLSVTIGRPASISC KSSQSLLDSDGKTYLYWLLQRPG QSPKRLIYLVSELDSGVPDRITG SGSGTDFTLKISRVEAEDLGVYY CWQGTHSPYTFGGGTKLEIK | SEQ ID No 46 |
| | | huVH 16a | QVQLVQSGAEVKKPGASVKVSCK ASGYTFTSYYMYWVRQAPGQGLE WMGIINPSNGGTSYAQKFQGRVT MTRDTSTSTVYMELSSLRSEDTA VYYCTRGGYYPFDYWGQGTTVTV SS | SEQ ID No 57 |
| | | huVH 16b | QVQLVQSGAEVKKPGASVKVSCK ASGYTFTSYYMHWVRQAPGQGLE WMGIINPSNGGTSYAQKFQGRVT MTRDTSTSTVYMELSSLRSEDTA VYYCTRGGYYPFDYWGQGTTVTV SS | SEQ ID No 58 |

TABLE 3-continued

| Hybridoma deposit | mAb | Amino acid sequences | | SEQ ID No |
|---|---|---|---|---|
| | | huVH 16c | QVQLVQSGAEVKKPGASVKVSCK ASGYTFTSYYMYWVRQAPGQGLE WMGEINPSNGGTNYAQKFQGRVT MTRDTSTSTVYMELSSLRSEDTA VYYCTRGGYYPFDYWGQGTTVTV SS | SEQ ID No 59 |
| | | huVL 16a | DVVMTQSPLSLPVTLGQPASISC RSSQSLLDSDGKTYLYWFQQRPG QSPRRLIYLVSNRDSGVPDRFSG SGSGTDFTLKISRVEAEDVGVYY CWQGTHSPYTFGQGTKLEIK | SEQ ID No 60 |
| | | huVL 16b | DVVMTQSPLSLPVTLGQPASISC RSSQSLLDSDGKTYLNWFQQRPG QSPRRLIYLVSNRDSGVPDRFSG SGSGTDFTLKISRVEAEDVGVYY CWQGTHSPYTFGQGTKLEIK | SEQ ID No 61 |
| | | huVL 16c | DVVMTQSPLSLPVTLGQPASISC RSSQSLLDSDGKTYLYWFQQRPG QSPRRLIYLVSERDSGVPDRFSG SGSGTDFTLKISRVEAEDVGVYY CWQGTHSPYTFGQGTKLEIK | SEQ ID No 62 |

TABLE 4

| Hybridoma deposit | mAb | Amino acid sequences | | SEQ ID No |
|---|---|---|---|---|
| 1B3B4F11 | mAb19 | VH CDR 1 | GYSITSDYA | SEQ ID No 22 |
| | | VH CDR 2 | ISFSGYT | SEQ ID No 23 |
| | | VH CDR 3 | AREVNYGDSYHFDY | SEQ ID No 24 |
| | | VL CDR 1 | SQHRTYT | SEQ ID No 25 |
| | | VL CDR 2 | VKKDGSH | SEQ ID No 26 |
| | | VL CDR 3 | GVGDAIKGQSVFV | SEQ ID No 27 |
| | | mVH 19 | DVQLQESGPGLVKPSQSLSLTCTV TGYSITSDYAWNWIRQFPGNKLEW MGYISFSGYTSYNPSLKSRISVTR DTSRNQFFLQLTSVTTEDTATYYC AREVNYGDSYHFDYWGQGTIVTVS S | SEQ ID No 47 |
| | | mVL 19 | QLALTQSSSASFSLGASAKLTCTL SSQHRTYTIEWYQQQSLKPPKYVM EVKKDGSHSTGHGIPDRFSGSSSG ADRYLSISNIQPEDEAIYICGVGD AIKGQSVFVFGGGTKVTVL | SEQ ID No 48 |
| | | huVH 19a | QVQLQESGPGLVKPSQTLSLTCTV SGYSITSDYAWNWIRQHPGKGLEW IGYISFSGYTYYNPSLKSRVTISV DTSKNQFSLKLSSVTAADTAVYYC AREVNYGDSYHFDYWGQGTLVTVS S | SEQ ID No 63 |
| | | huVH 19b | QVQLQESGPGLVKPSQTLSLTCTV SGYSITSDYAWSWIRQHPGKGLEW IGYISFSGYTYYNPSLKSRVTISV DTSKNQFSLKLSSVTAADTAVYYC AREVNYGDSYHFDYWGQGTLVTVS S | SEQ ID No 64 |
| | | huVH 19c | QVQLQESGPGLVKPSQTLSLTCTV SGYSITSDYAWNWIRQHPGKGLEW IGYISFSGYTSYNPSLKSRVTISV DTSKNQFSLKLSSVTAADTAVYYC | SEQ ID No 65 |

TABLE 4-continued

| Hybridoma deposit | mAb | Amino acid sequences | SEQ ID No |
|---|---|---|---|
| | | AREVNYGDSYHFDYWGQGTLVTVSS | |
| | huVL 19a | QLVLTQSPSASASLGASVKLTCTLSSQHRTYTIEWHQQQPEKGPRYLMKVKKDGSHSKGDGIPDRFSGSSSGAERYLTISSLQSEDEADYYCGVGDAIKGQSVFVFGGGTKVEIK | SEQ ID No 66 |
| | huVL 19b | QLVLTQSPSASASLGASVKLTCTLSSQHRTYTIAWHQQQPEKGPRYLMKVKKDGSHSKGDGIPDRFSGSSSGAERYLTISSLQSEDEADYYCGVGDAIKGQSVFVFGGGTKVEIK | SEQ ID No 67 |
| | huVL 19c | QLVLTQSPSASASLGASVKLTCTLSSQHRTYTIEWHQQQPEKGPRYLMEVKKDGSHSKGDGIPDRFSGSSSGAERYLTISSLQSEDEADYYCGVGDAIKGQSVFVFGGGTKVEIK | SEQ ID No 68 |

Examples of monoclonal antibodies that can be generated by using an immunogen comprising the amino-acid sequence "QGPWLEEEEEAYGWMDFGRRSAEDEN", (C-terminal part of progastrin) corresponding to the amino acid sequence 55-80 of human progastrin include, but are not restricted to antibodies designated as: mAb8 and mAb13 in the following Table 5 and 6. Experimental results of epitope mapping show that mAb13 do specifically bind an epitope within said hPG C-terminal amino acid sequence.

TABLE 5

| Hybridoma deposit | mAb | | Amino acid sequences | SEQ ID No |
|---|---|---|---|---|
| 1C10D3B9 | mAb8 | VH CDR 1 | GFTFTTYA | SEQ ID No 28 |
| | | VH CDR 2 | ISSGGTYT | SEQ ID No 29 |
| | | VH CDR 3 | ATQGNYSLDF | SEQ ID No 30 |
| | | VL CDR 1 | KSLRHTKGITF | SEQ ID No 31 |
| | | VL CDR 2 | QMS | SEQ ID No 32 |
| | | VL CDR 3 | AQNLELPLT | SEQ ID No 33 |
| | | mVH 8 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSS | SEQ ID No 49 |
| | | mVL 8 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIK | SEQ ID No 50 |
| | | VH hZ8CV1 | EVQLVESGGGLVKPGGSLRLSCAASGFTFTTYAMSWVRQAPGKGLEWVSSISSGGTYTYYADSVKGRFTISRDNAKNSLYLQMNSLRAEDTAVYYCATQGNYSLDFWGQGTTVTVSS | SEQ ID No 69 |
| | | VL hZ8CV1 | DIVMTQSPLSLPVTPGEPASISCRSSKSLRHTKGITFLYWYLQKPGQSPQLLIYQMSNRASGVPDRFSGSGSGTDFTLKISRVEAEDVGVYYCAQNLELPLTFGGGTKVEIK | SEQ ID No 70 |
| | | VH hZ8CV2 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSS | SEQ ID No 71 |

TABLE 5-continued

| Hybridoma deposit | mAb | Amino acid sequences | | SEQ ID No |
|---|---|---|---|---|
| | | VL hZ8CV2 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIK | SEQ ID No 72 |
| | | CH hZ8CV2 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | SEQ ID No 73 |
| | | CL hZ8CV2 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID No 74 |

TABLE 6

| Hybridoma deposit | mAb | Amino acid sequences | | SEQ ID No |
|---|---|---|---|---|
| 2C6C3C7 | mAb13 | VH CDR 1 | GFIFSSYG | SEQ ID No 34 |
| | | VH CDR 2 | INTFGDRT | SEQ ID No 35 |
| | | VH CDR 3 | ARGTGTY | SEQ ID No 36 |
| | | VL CDR 1 | QSLLDSDGKTY | SEQ ID No 37 |
| | | VL CDR 2 | LVS | SEQ ID No 38 |
| | | VL CDR 3 | WQGTHFPQT | SEQ ID No 39 |
| | | mVH 13 | EVQLVESGGGLVQPGGSLKLSCAASGFIFSSYGMSWVRQSPDRRLELVASINTFGDRTYYPDSVKGRFTISRDNAKNTLYLQMTSLKSEDTAIYYCARGTGTYWGQGTTLTVSS | SEQ ID No 51 |
| | | mVL 13 | DVVLTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPQTFGGGTKLEIK | SEQ ID No 52 |
| | | huVH 13a | EVQLVESGGGLVQPGGSLRLSCAASGFIFSSYGMSWVRQAPGKGLEWVANINTFGDRTYYVDSVKGRFTISRDNAKNSLYLQMNSLRAEDTAVYYCARGTGTYWGQGTLVTVSS | SEQ ID No 75 |
| | | huVH 13b | EVQLVESGGGLVQPGGSLRLSCAASGFIFSSYGMSWVRQAPGKGLEWVASINTFGDRTYYVDSVKGRFTISRDNA | SEQ ID No 76 |

TABLE 6-continued

| Hybridoma deposit | mAb | Amino acid sequences | SEQ ID No |
|---|---|---|---|
| | | KNSLYLQMNSLRAEDTAVYYCARGT GTYWGQGTLVTVSS | |
| | huVL 13a | DVVMTQSPLSLPVTLGQPASISCRS SQSLLDSDGKTYLNWFQQRPGQSPR RLIYLVSNRDSGVPDRFSGSGSGTD FTLKISRVEAEDVGVYYCWQGTHFP QTFGGGTKVEIK | SEQ ID No 77 |
| | huVL 13b | DVVMTQSPLSLPVTLGQPASISCRS SQSLLDSDGKTYLNWFQQRPGQSPR RLIYLVSKRDSGVPDRFSGSGSGTD FTLKISRVEAEDVGVYYCWQGTHFP QTFGGGTKVEIK | SEQ ID No 78 |

Other examples include anti-hPG monoclonal and/or polyclonal antibodies generated by using an immunogen comprising an amino acid sequence of SEQ ID N° 40.

The terms "N-terminal anti-hPG antibodies" and "C-terminal anti-hPG antibodies" designate antibodies binding to an epitope comprising amino acids located in the N-terminal part of hPG or to an epitope comprising amino acids located in the C-terminal part of hPG, respectively. Preferably, the term "N-terminal anti-hPG antibodies" refers to antibodies binding to an epitope located in a domain of progastrin whose sequence is represented by SEQ ID NO. 2. In another preferred embodiment, the term "C-terminal anti-hPG antibodies" refers to antibodies binding to an epitope located in a domain of progastrin whose sequence is represented by SEQ ID NO. 3.

The term "epitope" refers to a region of an antigen that is bound by an antibody. Epitopes may be defined as structural or functional. Functional epitopes are generally a subset of the structural epitopes and have those amino acids that directly contribute to the affinity of the interaction. Epitopes may also be conformational. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The determination of the epitope bound by an antibody may be performed by any epitope mapping technique, known by a man skilled in the art. An epitope may comprise different amino acids which located sequentially within the amino acid sequence of a protein. An epitope may also comprise amino acids which are not located sequentially within the amino acid sequence of a protein.

In a particular embodiment, said antibody is a monoclonal antibody selected in the group consisting of:

A monoclonal antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively, A monoclonal antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively, A monoclonal antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively, A monoclonal antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively, A monoclonal antibody comprising a heavy chain comprising at least one, preferentially at least two, preferentially at least three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively, and A monoclonal antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of methods known by a man skilled in the art.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

In a more particular embodiment, said antibody is a monoclonal antibody selected in the group consisting of:
A monoclonal antibody comprising a heavy chain of amino acid sequence SEQ ID N° 41 and a light chain of amino acid sequence SEQ ID N° 42;
A monoclonal antibody comprising a heavy chain of amino acid sequence SEQ ID N° 43 and a light chain of amino acid sequence SEQ ID N° 44;
A monoclonal antibody comprising a heavy chain of amino acid sequence SEQ ID N° 45 and a light chain of amino acid sequence SEQ ID N° 46;
A monoclonal antibody comprising a heavy chain of amino acid sequence SEQ ID N° 47 and a light chain of amino acid sequence SEQ ID N° 48;
A monoclonal antibody comprising a heavy chain of amino acid sequence SEQ ID N° 49 and a light chain of amino acid sequence SEQ ID N° 50; and
A monoclonal antibody comprising a heavy chain of amino acid sequence SEQ ID N° 51 and a light chain of amino acid sequence SEQ ID N° 52.

In a particular embodiment, the antibody of the present combination is a chimeric antibody.

A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass.

In another particular embodiment, the antibody of the present combination is a humanised antibody.

As used herein, the expression "humanised antibody" means an antibody that contains CDR regions derived from an antibody of nonhuman origin, the other parts of the antibody molecule being derived from one or several human antibodies. In addition, some of the skeleton segment residues (called FR for framework) can be modified to preserve binding affinity, according to techniques known by a man skilled in the art (Jones et al., Nature, 321:522-525, 1986). The goal of humanisation is a reduction in the immunogenicity of a xenogenic antibody, such as a murine antibody, for introduction into a human, while maintaining the full antigen binding affinity and specificity of the antibody.

The humanised antibodies of the invention or fragments of same can be prepared by techniques known to a person skilled in the art (such as, for example, those described in the documents Singer et al., J. Immun., 150:2844-2857, 1992). Such humanised antibodies are preferred for their use in methods involving in vitro diagnoses or preventive and/or therapeutic treatment in vivo. Other humanization techniques are also known to the person skilled in the art. Indeed, Antibodies can be humanised using a variety of techniques including CDR-grafting (EP 0 451 261; EP 0 682 040; EP 0 939 127; EP 0 566 647; U.S. Pat. Nos. 5,530,101; 6,180,370; 5,585,089; 5,693,761; 5,639,641; 6,054,297; 5,886,152; and 5,877,293), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. Sci. U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

In a more particular embodiment, said antibody is a humanised antibody selected in the group consisting of:
A humanised antibody comprising a heavy chain comprising at least one, preferentially at least two, preferentially three, of CDR-H1, CDR-H2 and CDR-H3 of amino acid sequences SEQ ID N° 4, 5 and 6, respectively, or sequences with at least 80%, preferably 85%, 90%, 95% and 98% identity after optimal alignment with sequences SEQ ID N° 4, 5 and 6, respectively, and a light chain comprising at least one, preferentially at least two, preferentially three, of CDR-L1, CDR-L2 and CDR-L3 of amino acid sequences SEQ ID N° 7, 8 and 9, respectively, or sequences with at least 80%, preferably 85%, 90%, 95% and 98% identity after optimal alignment with sequences SEQ ID N° 7, 8 and 9, respectively, A humanised antibody comprising a heavy chain comprising at least one, preferentially at least two, preferentially three, of CDR-H1, CDR-H2 and CDR-H3 of amino acid sequences SEQ ID N° 10, 11 and 12, respectively, or sequences with at least 80%, preferably 85%, 90%, 95% and 98% identity after optimal alignment with sequences SEQ ID N° 10, 11 and 12, respectively, and a light chain comprising at least one, preferentially at least two, preferentially three, of CDR-L1, CDR-L2 and CDR-L3 of amino acid sequences SEQ ID N° 13, 14 and 15, respectively, or sequences with at least 80%, preferably 85%, 90%, 95% and 98% identity after optimal alignment with sequences SEQ ID N° 13, 14 and 15, respectively, A humanised antibody comprising a heavy chain comprising at least one, preferentially at least two, preferentially three, of CDR-H1, CDR-H2 and CDR-H3 of amino acid sequences SEQ ID N° 16, 17 and 18, respectively, or sequences with at least 80%, preferably 85%, 90%, 95% and 98% identity after optimal alignment with sequences SEQ ID N° 16, 17 and 18, respectively, and a light chain comprising at least one, preferentially at least two, preferentially three, of CDR-L1, CDR-L2 and CDR-L3 of amino acid sequences SEQ ID N° 19, 20 and 21, respectively, or sequences with at least 80%, preferably 85%, 90%, 95% and 98% identity after optimal alignment with sequences SEQ ID N° 19, 20 and 21, respectively, A humanised antibody comprising a heavy chain comprising at least one, preferentially at least two, preferentially three, of CDR-H1, CDR-H2 and CDR-H3 of amino acid sequences SEQ ID N° 22, 23 and 24, respectively, or sequences with at least 80%, preferably 85%, 90%, 95% and 98% identity after optimal alignment with sequences SEQ ID N° 22, 23 and 24, respectively, and a light chain comprising at least one, preferentially at least two, preferentially three, of CDR-L1, CDR-L2 and CDR-L3 of amino acid sequences SEQ ID N° 25, 26 and 27, respectively, or sequences with at least 80%, preferably 85%, 90%, 95% and 98% identity after optimal alignment with sequences SEQ ID N° 25, 26 and 27, respectively, A humanised antibody comprising a heavy chain comprising at least one, preferentially at least two, preferentially three, of CDR-H1, CDR-H2 and CDR-H3 of amino acid sequences SEQ ID N° 28, 29 and 30, respectively, or sequences with at least 80%, preferably 85%, 90%, 95% and 98% identity after optimal alignment with sequences SEQ ID N° 28, 29 and 30, respectively, and a light chain comprising at least one, preferentially at least two, preferentially three, of CDR-L1, CDR-L2 and CDR-L3 of amino acid sequences SEQ ID N° 31, 32 and 33, respectively, or sequences with at least 80%, preferably 85%, 90%, 95% and 98% identity after optimal alignment with sequences SEQ ID N° 31, 32 and 33, respectively, and A humanised antibody comprising a heavy chain comprising at least one, preferentially at least two, preferentially three, of CDR-H1, CDR-H2 and CDR-H3 of amino acid sequences SEQ ID N° 34, 35 and 36, respectively, or sequences with at least 80%, preferably 85%, 90%, 95% and 98% identity after optimal alignment with sequences SEQ ID N° 34, 35 and 36, respectively, and a light chain comprising at least one, preferentially at least two, preferentially three, of CDR-L1, CDR-L2 and CDR-L3 of amino acid sequences SEQ ID N° 37, 38 and 39, respectively, or sequences with at least 80%, preferably 85%, 90%, 95% and 98% identity after optimal alignment with sequences SEQ ID N° 37, 38 and 39, respectively, wherein said antibody also comprises constant regions of the light-chain and the heavy-chain derived from a human antibody.

In another more particular embodiment, said antibody is a humanised antibody selected in the group consisting of:

A humanised antibody comprising a heavy chain variable region of amino acid sequence SEQ ID N° 53, and a light chain variable region of amino acid sequence SEQ ID N° 54;

A humanised antibody comprising a heavy chain variable region of amino acid sequence SEQ ID N° 55, and a light chain variable region of amino acid sequence SEQ ID N° 56;

A humanised antibody comprising a heavy chain variable region of amino acid sequence selected between SEQ ID N° 57, 58, and 59, and a light chain variable region of amino acid sequence selected between SEQ ID N° 60, 61, and 62;

A humanised antibody comprising a heavy chain variable region of amino acid sequence selected between SEQ ID N° 63, 64, and 65, and a light chain variable region of amino acid sequence selected between SEQ ID N° 66, 67, and 68;

A humanised antibody comprising a heavy chain variable region of amino acid sequence selected between SEQ ID N° 69 and 71, and a light chain variable region of amino acid sequence selected between SEQ ID N° 70 and 72; and A humanised antibody comprising a heavy chain variable region of amino acid sequence selected between SEQ ID N° 75 and 76, and a light chain variable region of amino acid sequence selected between SEQ ID N° 77 and 78;

wherein said antibody also comprises constant regions of the light-chain and the heavy-chain derived from a human antibody.

More preferably, said antibody comprises a heavy chain variable region of amino acid sequence SEQ ID N° 71 and a light chain variable region of amino acid sequence SEQ ID N° 72, said antibody also comprising constant regions of the light-chain and the heavy-chain derived from a human antibody.

Even more preferably, said antibody comprises a heavy chain of amino acid sequence SEQ ID N° 73 and a light chain of amino acid sequence SEQ ID N° 74.

Antibody Fragments

Fragments of an antibody, notably antigen-binding fragments thereof, are also encompassed in the invention.

"Antibody fragments" comprise a portion of a full-length antibody, generally the antigen binding or variable region thereof. Examples of antibody fragments include Fab, Fab', F(ab')2, Fv fragments and Scfv; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "antigen-binding domain" of an antibody (or "antigen-binding fragment") refers to one or more fragments of an antibody that retain the ability to specifically bind to an antigen (e.g., hPG). It has been shown that the antigen-binding function of an antibody can be performed by fragments of a full-length antibody. Examples of binding fragments encompassed within the term "antigen-binding domain" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) *Nature* 341: 544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding domain" of an antibody.

These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

Antibody Derivatives

The anti-hPG antibodies of the present invention can be further modified to contain additional non-proteinaceous moieties that are known in the art and readily available. In particular, included herein are anti-hPG monoclonal antibodies which are derivatized, covalently modified, or conjugated to other molecules, for use in diagnostic and therapeutic applications. For example, but not by way of limitation, derivatized antibodies include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivative can contain one or more non-classical amino acids.

Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In a specific example, the anti-hPG antibodies of the present disclosure can be attached to Poly(ethyleneglycol) (PEG) moieties. In a specific embodiment, the antibody is an antibody fragment and the PEG moieties are attached through any available amino acid side-chain or terminal amino acid functional group located in the antibody fragment, for example any free amino, imino, thiol, hydroxyl or carboxyl group. Such amino acids can occur naturally in the antibody fragment or can be engineered into the fragment using recombinant DNA methods. See, for example U.S. Pat. No. 5,219,996. Multiple sites can be used to attach two or more PEG molecules. PEG moieties can be covalently linked through a thiol group of at least one cysteine residue located in the antibody fragment. Where a thiol group is used as the point of attachment, appropriately activated effector moieties, for example thiol selective derivatives such as maleimides and cysteine derivatives, can be used.

In a specific example, an anti-hPG antibody conjugate is a modified Fab' fragment which is PEGylated, i.e., has PEG (poly(ethyleneglycol)) covalently attached thereto, e.g., according to the method disclosed in EP0948544. See also Poly(ethyleneglycol) Chemistry, Biotechnical and Biomedical Applications, (J. Milton Harris (ed.), Plenum Press, New York, 1992); Poly(ethyleneglycol) Chemistry and Biological Applications, (J. Milton Harris and S. Zalipsky, eds., American Chemical Society, Washington D.C., 1997); and Bioconjugation Protein Coupling Techniques for the Biomedical Sciences, (M. Aslam and A. Dent, eds., Grove Publishers, New York, 1998); and Chapman, 2002, Advanced Drug Delivery Reviews 54:531-545. PEG can be attached to a cysteine in the hinge region. In one example, a PEG-modified Fab' fragment has a maleimide group covalently linked to a single thiol group in a modified hinge region. A lysine residue can be covalently linked to the maleimide group and to each of the amine groups on the lysine residue can be attached a methoxypoly(ethyleneglycol) polymer having a molecular weight of approximately 20,000 Da. The total molecular weight of the PEG attached to the Fab' fragment can therefore be approximately 40,000 Da.

In another embodiment, conjugates of an antibody and non-proteinaceous moiety that may be selectively heated by exposure to radiation are provided. In one embodiment, the non-proteinaceous moiety is a carbon nanotube (Kam et al, Proc. Natl. Acad. Sci. USA 102: 11600-11605 (2005)). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

Immunoconjugates

In another aspect, the invention also provides immunoconjugates (interchangeably referred to as "antibody-drug conjugates," or "ADCs") comprising an anti-hPG antibody as described herein, said antibody being conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate).

Immunoconjugates have been used for the local delivery of cytotoxic agents, i.e., drugs that kill or inhibit the growth or proliferation of cells, in the treatment of cancer (Lambert, J. (2005) Curr. Opinion in Pharmacology 5:543-549; Wu et al (2005) Nature Biotechnology 23(9): 1137-1146; Payne, G. (2003) i 3:207-212; Syrigos and Epenetos (1999) Anticancer Research 19:605-614; Niculescu-Duvaz and Springer (1997) Adv. Drug Deliv. Rev. 26:151-172; U.S. Pat. No. 4,975,278). Immunoconjugates allow for the targeted delivery of a drug moiety to a tumour, and intracellular accumulation therein, where systemic administration of unconjugated drugs may result in unacceptable levels of toxicity to normal cells as well as the tumour cells sought to be eliminated (Baldwin et al, Lancet (Mar. 15, 1986) pp. 603-05; Thorpe (1985) "Antibody Carriers Of Cytotoxic Agents In Cancer Therapy: A Review," in Monoclonal Antibodies '84: Biological And Clinical Applications (A. Pinchera et al., eds) pp. 475-506. Both polyclonal antibodies and monoclonal antibodies have been reported as useful in these strategies (Rowland et al., (1986) Cancer Immunol. Immunother. 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) J. Nat. Cancer Inst. 92(19): 1573-1581; Mandler et al (2000) Bioorganic a Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, Phytolaca americana proteins (PAPI, PAPII, and PAP-S), *Momordica charantia* inhibitor, curcin, crotin, sapaonaria *officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol)propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et ah, Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

The immunoconjugate of the invention may further comprise a linker.

"Linker", "Linker Unit", or "link" means a chemical moiety comprising a covalent bond or a chain of atoms that covalently attaches a binding protein to at least one cytotoxic agent.

Linkers may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non-cleavable" or "cleavable".

Nucleic Acids and Expression Systems

The present disclosure encompasses polynucleotides encoding immunoglobulin light and heavy chain genes for antibodies, notably anti-hPG antibodies, vectors comprising such nucleic acids, and host cells capable of producing the antibodies of the disclosure.

In a first aspect, the present invention relates to one or more polynucleotides encoding an antibody, notably an antibody capable of binding specifically to progastrin as described above.

A first embodiment provides a polynucleotide encoding the heavy chain of an anti-hPG antibody described above. Preferably, said heavy chain comprises three heavy-chain CDRs of sequence SEQ ID NOS. 4, 5 and 6. More preferably, said heavy chain comprises a heavy chain comprising the variable region of sequence SEQ ID NO. 14. Even more preferably, said heavy chain has a complete sequence SEQ ID NO. 16.

In another embodiment, the polynucleotide encodes the light chain of an anti-hPG antibody described above. Preferably, said heavy chain comprises three heavy-chain CDRs of sequence SEQ ID NOS. 7, 8 and 9. More preferably, said heavy chain comprises a heavy chain comprising the variable region of sequence SEQ ID NO. 15. Even more preferably, said heavy chain has a complete sequence SEQ ID NO. 17.

According to the invention, a variety of expression systems may be used to express the antibody of the invention. In one aspect, such expression systems represent vehicles by which the coding sequences of interest may be produced and subsequently purified, but also represent cells which may, when transiently transfected with the appropriate nucleotide coding sequences, express an IgG antibody in situ.

The invention provides vectors comprising the polynucleotides described above. In one embodiment, the vector contains a polynucleotide encoding a heavy chain of the antibody of interest (e.g., an anti-hPG antibody). In another embodiment, said polynucleotide encodes the light chain of the antibody of interest (e.g., an anti-hPG antibody). The invention also provides vectors comprising polynucleotide molecules encoding fusion proteins, modified antibodies, antibody fragments, and probes thereof.

In order to express the heavy and/or light chain of the antibody of interest (e.g., an anti-hPG antibody), the polynucleotides encoding said heavy and/or light chains are inserted into expression vectors such that the genes are operatively linked to transcriptional and translational sequences.

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to affect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Certain vectors are capable of directing the expression of genes to which they are operatively linked. Such vectors are referred to herein as "recombinant expression vectors" (or simply, "expression vectors"). In general, expression vectors of utility in recombinant DNA techniques are in the form of plasmids. In the present specification, "plasmid" and "vector" may be used interchangeably as the plasmid is the most commonly used form of vector. However, the invention is intended to include such forms of expression vectors, such as bacterial plasmids, YACs, cosmids, retrovirus, EBV-derived episomes, and all the other vectors that the skilled man will know to be convenient for ensuring the expression of the heavy and/or light chains of the antibody of interest (e.g., an anti-hPG antibody). The skilled man will realize that the polynucleotides encoding the heavy and the light chains can be cloned into different vectors or in the same vector. In a preferred embodiment, said polynucleotides are cloned into two vectors.

Polynucleotides of the invention and vectors comprising these molecules can be used for the transformation of a suitable host cell. The term "host cell", as used herein, is intended to refer to a cell into which a recombinant expression vector has been introduced in order to express the antibody of interest (e.g., an anti-hPG antibody). It should be understood that such terms are intended to refer not only to the particular subject cell but also to the progeny of such a cell. Because certain modifications may occur in succeeding generations due to either mutation or environmental influences, such progeny may not, in fact, be identical to the parent cell, but are still included within the scope of the term "host cell" as used herein.

Transformation can be performed by any known method for introducing polynucleotides into a cell host. Such methods are well known of the man skilled in the art and include dextran-mediated transformation, calcium phosphate precipitation, polybrene-mediated transfection, protoplast fusion, electroporation, encapsulation of the polynucleotide into liposomes, biolistic injection and direct microinjection of DNA into nuclei.

The host cell may be co-transfected with one or more expression vectors. For example, a host cell can be transfected with a vector encoding both the heavy chain and the light chain of the antibody of interest (e.g., an anti-hPG antibody), as described above. Alternatively, the host cell can be transformed with a first vector encoding the heavy chain of the antibody of interest (e.g., an anti-hPG antibody), and with a second vector encoding the light chain of said antibody. Mammalian cells are commonly used for the expression of a recombinant therapeutic immunoglobulins, especially for the expression of whole recombinant antibodies. For example, mammalian cells such as HEK293 or CHO cells, in conjunction with a vector, containing the expression signal such as one carrying the major intermediate early gene promoter element from human cytomegalovirus, are an effective system for expressing the humanised anti-hPG antibody of the invention (Foecking et al., 1986, *Gene* 45:101; Cockett et al., 1990, *Bio/Technology* 8: 2).

In addition, a host cell may be chosen which modulates the expression of the inserted sequences, or modifies and processes the gene product in the specific fashion desired. Such modifications (e.g., glycosylation) and processing of protein products may be important for the function of the protein. Different host cells have features and specific mechanisms for the post-translational processing and modification of proteins and gene products. Appropriate cell lines or host systems are chosen to ensure the correct modification and processing of the expressed antibody of interest. Hence, eukaryotic host cells which possess the cellular machinery for proper processing of the primary transcript, glycosylation of the gene product may be used. Such mammalian host cells include, but are not limited to, CHO, COS, HEK293, NS/0, BHK, Y2/0, 3T3 or myeloma cells (all these cell lines are available from public depositories such as the Collection Nationale des Cultures de Microorganismes, Paris, France, or the American Type Culture Collection, Manassas, Va., U.S.A.).

For long-term, high-yield production of recombinant proteins, stable expression is preferred. In one embodiment of the invention, cell lines which stably express the antibody may be engineered. Rather than using expression vectors which contain viral origins of replication, host cells are transformed with DNA under the control of the appropriate expression regulatory elements, including promoters, enhancers, transcription terminators, polyadenylation sites, and other appropriate sequences known to the person skilled in art, and a selectable marker. Following the introduction of the foreign DNA, engineered cells may be allowed to grow for one to two days in an enriched media, and then are moved to a selective media. The selectable marker on the recombinant plasmid confers resistance to the selection and allows cells to stably integrate the plasmid into a chromosome and be expanded into a cell line. Other methods for constructing stable cell lines are known in the art. In particular, methods for site-specific integration have been developed. According to these methods, the transformed DNA under the control of the appropriate expression regulatory elements, including promoters, enhancers, transcription terminators, polyadenylation sites, and other appropriate sequences is integrated in the host cell genome at a specific target site which has previously been cleaved (Moele et al., Proc. Natl. Acad. Sci. U.S.A., 104(9): 3055-3060; U.S. Pat. Nos. 5,792,632; 5,830,729; 6,238,924; WO 2009/054985; WO 03/025183; WO 2004/067753).

A number of selection systems may be used according to the invention, including but not limited to the Herpes simplex virus thymidine kinase (Wigler et al., Cell 11:223, 1977), hypoxanthine-guanine phosphoribosyltransferase (Szybalska et al., Proc Natl Acad Sci USA 48: 202, 1992), glutamate synthase selection in the presence of methionine sulfoximide (Adv Drug Del Rev, 58: 671, 2006, and website or literature of Lonza Group Ltd.) and adenine phosphoribosyltransferase (Lowy et al., Cell 22: 817, 1980) genes in tk, hgprt or aprt cells, respectively. Also, antimetabolite resistance can be used as the basis of selection for the following genes: dhfr, which confers resistance to methotrexate (Wigler et al., Proc Natl Acad Sci USA 77: 357, 1980); gpt, which confers resistance to mycophenolic acid (Mulligan et al., Proc Natl Acad Sci USA 78: 2072, 1981); neo, which confers resistance to the aminoglycoside, G-418 (Wu et al., Biotherapy 3: 87, 1991); and hygro, which confers resistance to hygromycin (Santerre et al., Gene 30: 147, 1984). Methods known in the art of recombinant DNA technology may be routinely applied to select the desired recombinant clone, and such methods are described, for example, in Ausubel et al., eds., Current Protocols in Molecular Biology, John Wiley & Sons (1993). The expression levels of an antibody can be increased by vector amplification. When a marker in the vector system expressing an antibody is amplifiable, an increase in the level of inhibitor present in the culture will increase the number of copies of the marker gene. Since the amplified region is associated with the gene encoding the IgG antibody of the invention, production of said antibody will also increase (Crouse et al., *Mol Cell Bio* 3: 257, 1983). Alternative methods of expressing the gene of the invention exist and are known to the person of skills in the art. For example, a modified zinc finger protein can be engineered that is capable of binding the expression regulatory elements upstream of the gene of the invention; expression of the said engineered zinc finger protein (ZFN) in the host cell of the invention leads to increases in protein production (see e.g. Reik et al., *Biotechnol. Bioeng.*, 97(5): 1180-1189, 2006). Moreover, ZFN can stimulate the integration of a DNA into a predetermined genomic location, resulting in high-efficiency site-specific gene addition (Moehle et al, *Proc Natl Acad Sci USA,* 104: 3055, 2007).

The antibody of interest (e.g., an anti-hPG antibody) may be prepared by growing a culture of the transformed host cells under culture conditions necessary to express the desired antibody. The resulting expressed antibody may then be purified from the culture medium or cell extracts. Soluble forms of the antibody of interest (e.g., an anti-hPG antibody) can be recovered from the culture supernatant. It may then be purified by any method known in the art for purification of an immunoglobulin molecule, for example, by chromatography (e.g., ion exchange, affinity, particularly by Protein A affinity for Fc, and so on), centrifugation, differential solubility or by any other standard technique for the purification of proteins. Suitable methods of purification will be apparent to a person of ordinary skills in the art.

Another aspect of the invention thus relates to a method for the production of an antibody (e.g., an anti-hPG antibody) described herein, said method comprising the steps of:
 a) growing the above-described host cell in a culture medium under suitable culture conditions; and
 b) recovering the antibody (e.g., an anti-hPG antibody), from the culture medium or from said cultured cells.

Pharmaceutical Compositions

The combination of anti-hPG monoclonal antibodies and immune checkpoint inhibitors can be formulated in compositions. Optionally, the compositions can comprise one or more additional therapeutic agents, such as the third therapeutic agents described below. The compositions will usually be supplied as part of a sterile, pharmaceutical composition that will normally include a pharmaceutically acceptable carrier and/or excipient. In another aspect, the invention thus provides a pharmaceutical composition comprising the anti-hPG antibody, an immune checkpoint inhibitor, and a pharmaceutical acceptable vehicle and/or an excipient.

This composition can be in any suitable form (depending upon the desired method of administering it to a patient). As used herein, "administering" is meant a method of giving a dosage of a compound (e.g., an anti-hPG antibody and/or an immune checkpoint inhibitor, as described above) or a composition (e.g., a pharmaceutical composition, e.g., a pharmaceutical composition containing an anti-hPG antibody and/or an immune checkpoint inhibitor, as described above) to a subject. The compositions utilized in the methods described herein can be administered, for example, intravitreally (e.g., by intravitreal injection), by eye drop, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumourally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated). The most suitable route for administration in any given case will depend on the particular antibody, the subject, and the nature and severity of the disease and the physical condition of the subject. The anti-hPG antibody and/or the immune checkpoint inhibitor can be formulated as an aqueous solution and administered by subcutaneous injection.

Pharmaceutical compositions can be conveniently presented in unit dose forms containing a predetermined amount of an anti-hPG antibody and/or an immune checkpoint inhibitor per dose. Such a unit can contain for example but without limitation 5 mg to 5 g, for example 10 mg to 1 g, or 20 to 50 mg. Pharmaceutically acceptable carriers for use in the disclosure can take a wide variety of forms depending, e.g., on the condition to be treated or route of administration.

Pharmaceutical compositions of the disclosure can be prepared for storage as lyophilized formulations or aqueous solutions by mixing the antibody having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188, etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The present invention is further directed to a pharmaceutical composition comprising at least:
  i) one anti-hPG antibody and
  ii) an immune checkpoint inhibitor,
  as combination products for simultaneous, separate or sequential use.

"Simultaneous use" as used herein refers to the administration of the two compounds of the composition according to the invention in a single and identical pharmaceutical form.

"Separate use" as used herein refers to the administration, at the same time, of the two compounds of the composition according to the invention in distinct pharmaceutical forms.

"Sequential use" as used herein refers to the successive administration of the two compounds of the composition according to the invention, each in a distinct pharmaceutical form.

Compositions of anti-hPG antibodies and immune checkpoint inhibitors can be administered singly, as mixtures of one or more anti-hPG monoclonal antibodies and/or one or more immune checkpoint inhibitors, in mixture or combination with other agents useful for treating cancer, notably CRC, or adjunctive to other therapy for cancer, notably CRC. Examples of suitable combination and adjunctive therapies are provided below.

Encompassed by the present disclosure are pharmaceutical kits containing neutralising anti-hPG antibodies (including antibody conjugates) and immune checkpoint inhibitors described herein. The pharmaceutical kit is a package comprising a neutralising anti-hPG antibody and/or immune checkpoint inhibitor (e.g., either in lyophilized form or as an aqueous solution) and one or more of the following:

A third therapeutic agent, for example as described below;
A device for administering the neutralising anti-hPG antibody and/or immune checkpoint inhibitor, for example a pen, needle and/or syringe; and
Pharmaceutical grade water or buffer to resuspend the antibody if the antibody and/or the inhibitor is in lyophilized form.

Each unit dose of the anti-hPG antibody and/or immune checkpoint inhibitor can be packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Effective Dosages

The combinations of anti-hPG antibodies and immune checkpoint inhibitors will generally be used in an amount effective to achieve the intended result, for example an amount effective to treat cancer in a subject in need thereof. Pharmaceutical compositions comprising anti-hPG antibodies and/or immune checkpoint inhibitors can be administered to patients (e.g., human subjects) at therapeutically effective dosages.

The term "therapeutically effective dosage" means an amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. More specifically, a "therapeutically effective" dosage as used herein is an amount that confers a therapeutic benefit. A therapeutically effective dosage is also one in which any toxic or detrimental effects of the agent are outweighed by the therapeutically beneficial effects. In the context of CRC therapy, a therapeutic benefit means any amelioration of cancer, including any one of, or combination of, halting or slowing the progression of cancer (e.g., from one stage of cancer to the next), halting or delaying aggravation or deterioration of the symptoms or signs of cancer, reducing the severity of cancer, inducing remission of cancer, inhibiting tumour cell proliferation, tumour size, or tumour number, or reducing PG serum levels.

Determination of the effective amount is well within the capability of those skilled in the art, especially in light of the detailed disclosure provided herein. Toxicity and therapeutic efficacy of a compound or a conjugate can be determined by standard pharmaceutical procedures in cell cultures and in experimental animals. The effective amount of present combination or other therapeutic agent to be administered to a subject will depend on the stage, category and status of the multiple myeloma and characteristics of the subject, such as general health, age, sex, body weight and drug tolerance. The effective amount of the present combination or other therapeutic agent to be administered will also depend on administration route and dosage form. Dosage amount and interval can be adjusted individually to provide plasma levels of the active compound that are sufficient to maintain desired therapeutic effects.

The amount of the combination of anti-hPG antibody and immune checkpoint inhibitor administered will depend on a variety of factors, including the nature and stage of the CRC being treated, the form, route and site of administration, the therapeutic regimen (e.g., whether another therapeutic agent is used), the age and condition of the particular subject being treated, the sensitivity of the patient being treated to anti-hPG antibodies and/or and immune checkpoint inhibitors. The appropriate dosage can be readily determined by a person skilled in the art. Ultimately, a physician will determine appropriate dosages to be used. This dosage can be repeated as often as appropriate. If side effects develop the amount and/or frequency of the dosage can be altered or reduced, in accordance with normal clinical practice. The proper dosage and treatment regimen can be established by monitoring the progress of therapy using conventional techniques known to the people skilled of the art.

Effective dosages can be estimated initially from in vitro assays. For example, an initial dose for use in animals may be formulated to achieve a circulating blood or serum concentration of humanised anti-hPG antibody that is at or above the binding affinity of the antibody for progastrin as measured in vitro. Likewise, an initial dose for use in animals may be formulated to achieve a circulating blood or serum concentration of immune checkpoint inhibitor that is at or above the binding affinity of the inhibitor for the corresponding immune checkpoint protein as measured in vitro. Calculating dosages to achieve such circulating blood or serum concentrations taking into account the bioavailability of the particular antibody is well within the capabilities of skilled artisans. For guidance, the reader is referred to Fingl & Woodbury, "General Principles" in *Goodman and Gilman's The Pharmaceutical Basis of Therapeutics*, Chapter 1, latest edition, Pagamonon Press, and the references cited therein.

Initial dosages can be estimated from in vivo data, such as animal models. Animal models useful for testing the efficacy of compounds to treat CRC are well known in the art. Additionally, animal models of CRC are described in the Examples below. Ordinarily skilled artisans can routinely adapt such information to determine dosages suitable for human administration.

The effective dose of a combination of anti-hPG antibody and immune checkpoint inhibitor as described herein can range from about 0.001 to about 75 mg/kg per single (e.g., bolus) administration, multiple administrations or continuous administration, or to achieve a serum concentration of 0.01-5000 µg/ml serum concentration per single (e.g., bolus) administration, multiple administrations or continuous administration, or any effective range or value therein depending on the condition being treated, the route of administration and the age, weight and condition of the subject. In a certain embodiment, each dose can range from about 0.5 µg to about 50 µg per kilogram of body weight, for example from about 3 µg to about 30 µg per kilogram body weight.

Amount, frequency, and duration of administration will depend on a variety of factors, such as the patient's age, weight, and disease condition. A therapeutic regimen for administration can continue for 2 weeks to indefinitely, for 2 weeks to 6 months, from 3 months to 5 years, from 6 months to 1 or 2 years, from 8 months to 18 months, or the like. Optionally, the therapeutic regimen provides for repeated administration, e.g., once daily, twice daily, every two days, three days, five days, one week, two weeks, or one month. The repeated administration can be at the same dose or at a different dose. The administration can be repeated once, twice, three times, four times, five times, six times, seven times, eight times, nine times, ten times, or more. A therapeutically effective amount of a combination of anti-hPG antibody and immune checkpoint inhibitor can be administered as a single dose or over the course of a therapeutic regimen, e.g., over the course of a week, two weeks, three weeks, one month, three months, six months, one year, or longer.

Therapeutic Methods

The ability of the present combinations of anti-hPG antibodies and immune checkpoint inhibitors to block PG-dependent responses, including cell proliferation, and to improve the response to immunotherapy, makes them useful for treating cancer. Accordingly, an aspect of the present invention thus relates to the present combination of anti-hPG antibody and immune checkpoint inhibitor as a medicament.

In another aspect, the present disclosure provides methods of treating cancer in a patient in need thereof. Cancers which can be treated with the combination of the invention are notably the cancers which are dependent upon progastrin for growth and/or proliferation. Preferably, the progastrin-dependent cancer is colorectal cancer (CRC). Generally, the methods comprise administering to the patient a therapeutically effective amount of the combination of anti-hPG antibody and immune checkpoint inhibitor described herein. In another embodiment, the present disclosure provides the combination of anti-hPG antibody and immune checkpoint inhibitor described herein for use in the treatment of CRC.

A "subject" or "patient" to whom the present combination of anti-hPG antibody and immune checkpoint inhibitor is administered is preferably a mammal such as a non-primate (e.g., cow, pig, horse, cat, dog, rat, etc.) or a primate (e.g., monkey or human). The subject or patient can be a human, such as an adult patient or a paediatric patient.

Patients suitable for anti-hPG antibody/immune checkpoint inhibitor combination therapy are patients diagnosed with CRC. The CRC can be of any type and at any clinical stage or manifestation. Suitable subjects include patients with CRC tumours (operable or inoperable), patients whose tumours have been surgically removed or resected, patients with a CRC tumour comprising cells carrying a mutation in an oncogene, such as, for example, RAS or APC, patients who have received or receive other therapy for CRC in combination with or adjunctive to humanised anti-hPG antibody therapy. Other therapy for CRC includes, but is not limited to, chemotherapeutic treatment, radiation therapy, surgical resection, and treatment with one or more other therapeutic antibodies, as detailed below.

According to other embodiments, combinations of anti-hPG antibodies and immune checkpoint inhibitors as disclosed herein are administered in a composition to a subject in need of prevention of metastatic colorectal cancer in a therapeutically effective amount. Such subjects include, but are not limited to those determined to have primary colorectal cancer but in whom the cancer is not known to have spread to distant tissues or organs. In certain embodiments of these methods, the anti-hPG antibodies are humanised anti-hPG antibodies.

According to yet other embodiments, the combinations of anti-hPG antibodies and immune checkpoint inhibitors as disclosed herein are administered in a composition to a subject in need of prevention for recurrence of metastatic colorectal cancer in a therapeutically effective amount. Such subjects include, but are not limited to those who were previously treated for primary or metastatic colorectal cancer, after which treatment such cancer apparently disappeared. In certain embodiments of these methods, the anti-hPG antibodies are humanised anti-hPG antibodies.

According to other embodiments, combinations of anti-hPG antibodies and immune checkpoint inhibitors as disclosed herein are administered in a composition to a subject in need of inhibition of the growth of colorectal cancer stem cells in a therapeutically effective amount. Such subjects include, but are not limited to those having a colorectal cancer the growth or metastasis of which is at least partly attributable to the presence within it of cancer stem cells. Other embodiments provide for methods of preventing or inhibiting the growth of colorectal cancer stem cells by contacting such stem cells with an amount of an anti-PG antibody/immune checkpoint inhibitor composition effective to prevent or inhibit the growth of such cells. Such methods can be carried out in vitro or in vivo. In certain embodiments of these methods, the anti-hPG antibodies are humanised anti-hPG antibodies.

Anti-hPG antibody/immune checkpoint inhibitor combination therapy can be combined with, or adjunctive to, one or more other treatments. Other treatments include, without limitation, chemotherapeutic treatment, radiation therapy, surgical resection, and antibody therapy, as described herein.

Anti-hPG antibody/immune checkpoint inhibitor combination therapy can be adjunctive to other treatment, including surgical resection.

Combination therapy as provided herein involves the administration of at least two agents to a patient, the first of which is an anti-hPG antibody/immune checkpoint inhibitor combination of the disclosure, and the second of which is another therapeutic agent. According to this embodiment, the invention relates to the anti-hPG antibody/immune checkpoint inhibitor combination described above, for the treatment of CRC, wherein said combination is administered with said other therapeutic agent. The anti-hPG antibody/immune checkpoint inhibitor combination and the other therapeutic agent can be administered simultaneously, successively, or separately.

A "therapeutic agent" encompasses biological agents, such as an antibody, a peptide, a protein, an enzyme, and chemotherapeutic agents. The therapeutic agent also encompasses immuno-conjugates of cell-binding agents (CBAs) and chemical compounds, such as antibody-drug conjugates (ADCs). The drug in the conjugates can be a cytotoxic agent, such as one described herein.

As used herein, the anti-hPG antibody/immune checkpoint inhibitor combination and the other therapeutic agent are said to be administered successively if they are administered to the patient on the same day, for example during the same patient visit. Successive administration can occur 1, 2, 3, 4, 5, 6, 7 or 8 hours apart. In contrast, the combination of the disclosure and the other therapeutic agent are said to be administered separately if they are administered to the patient on the different days, for example, the combination of the disclosure and the other therapeutic agent can be administered at a 1-day, 2-day or 3-day, one-week, 2-week or monthly intervals. In the methods of the present disclosure, administration of the combination of the disclosure can precede or follow administration of the other therapeutic agent.

As a non-limiting example, the instant combination and other therapeutic agent can be administered concurrently for a period of time, followed by a second period of time in which the administration of the humanised anti-hPG antibody of the disclosure and the other therapeutic agent is alternated.

Combination therapies of the present disclosure can result in a greater than additive, or a synergistic, effect, providing therapeutic benefits where neither the anti-hPG antibody/immune checkpoint inhibitor combination nor other therapeutic agent is administered in an amount that is, alone, therapeutically effective. Thus, such agents can be administered in lower amounts, reducing the possibility and/or severity of adverse effects.

In a preferred embodiment, the other therapeutic agent is a chemotherapeutic agent. A "chemotherapeutic agent," as used herein, refers to a substance which, when administered to a subject, treats or prevents the development of cancer in the subject's body.

Chemotherapeutic agents include, but are not limited to, alkylating agents, anti-metabolites, anti-tumour antibiotics, mitotic inhibitors, chromatin function inhibitors, anti-angiogenesis agents, anti-estrogens, anti-androgens or immunomodulators.

"Alkylating agent" refers to any substance which can cross-link or alkylate any molecule, preferably nucleic acid (e.g., DNA), within a cell. Examples of alkylating agents include nitrogen mustard such as mechlorethamine, chlorambucol, melphalen, chlorydrate, pipobromen, prednimustin, disodic-phosphate or estramustine; oxazophorins such as cyclophosphamide, altretamine, trofosfamide, sulfofosfamide or ifosfamide; aziridines or imine-ethylénes such as thiotepa, triethylenamine or altetramine; nitrosourea such as carmustine, streptozocin, fotemustin or lomustine; alkylesulfonates such as busulfan, treosulfan or improsulfan; triazenes such as dacarbazine; or platinum complexes such as cis-platinum, oxaliplatin and carboplatin.

"Anti-metabolites" refer to substances that block cell growth and/or metabolism by interfering with certain activities, usually DNA synthesis. Examples of anti-metabolites include methotrexate, 5-fluoruracil, floxuridine, 5-fluorodeoxyuridine, capecitabine, cytarabine, fludarabine, cytosine arabinoside, 6-mercaptopurine (6-MP), 6-thioguanine (6-TG), chlorodesoxyadenosine, 5-azacytidine, gemcitabine, cladribine, deoxycoformycin and pentostatin.

"Anti-tumour antibiotics" refer to compounds which may prevent or inhibit DNA, RNA and/or protein synthesis. Examples of anti-tumour antibiotics include doxorubicin, daunorubicin, idarubicin, valrubicin, mitoxantrone, dactinomycin, mithramycin, plicamycin, mitomycin C, bleomycin, and procarbazine.

"Mitotic inhibitors" prevent normal progression of the cell cycle and mitosis. In general, microtubule inhibitors or taxoides such as paclitaxel and docetaxel are capable of inhibiting mitosis. Vinca alkaloid such as vinblastine, vincristine, vindesine and vinorelbine are also capable of inhibiting mitosis.

"Chromatin function inhibitors" or "topoisomerase inhibitors" refer to substances which inhibit the normal function of chromatin modeling proteins such as topoisomerase I or topoisomerase II. Examples of chromatin function inhibitors include, for topoisomerase I, camptothecine and its derivatives such as topotecan or irinotecan, and, for topoisomerase II, etoposide, etoposide phosphate and teniposide.

"Anti-angiogenesis agent" refers to any drug, compound, substance or agent which inhibits growth of blood vessels. Exemplary anti-angiogenesis agents include, but are by no means limited to, razoxin, marimastat, batimastat, prinomastat, tanomastat, ilomastat, CGS-27023A, halofuginon, COL-3, neovastat, BMS-275291, thalidomide, CDC 501, DMXAA, L-651582, squalamine, endostatin, SU5416, SU6668, interferon-alpha, EMD121974, interleukin-12, IM862, angiostatin and vitaxin.

"Anti-oestrogen" or "anti-estrogenic agent" refer to any substance which reduces, antagonizes or inhibits the action of estrogen. Examples of anti-oestrogen agents are tamoxifen, toremifene, raloxifene, droloxifene, iodoxyfene, anastrozole, letrozole, and exemestane.

"Anti-androgens" or "anti-androgen agents" refer to any substance which reduces, antagonizes or inhibits the action of an androgen. Examples of anti-androgens are flutamide, nilutamide, bicalutamide, sprironolactone, cyproterone acetate, finasteride and cimitidine.

"Immunomodulators" are substances which stimulate the immune system.

Examples of immunomodulators include interferon, interleukin such as aldesleukine, OCT-43, denileukin diflitox and interleukin-2, tumoural necrose fators such as tasonermine or others immunomodulators such as lentinan, sizofiran, roquinimex, pidotimod, pegademase, thymopentine, poly I:C or levamisole in conjunction with 5-fluorouracil.

For more detail, the person of skill in the art could refer to the manual edited by the "Association Française des Enseignants de Chimie Thérapeutique" and entitled "Traité de chimie thérapeutique", vol. 6, Médicaments antitumouraux et perspectives dans le traitement des cancers, edition TEC & DOC, 2003.

It can also be mentioned as chemical agents or cytotoxic agents, all kinase inhibitors such as, for example, gefitinib or erlotinib.

More generally, examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), anti-mitotic agents, cis-dichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, oxaliplatin, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, tegafur, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

The anti-hPG antibody/immune checkpoint inhibitor combinations disclosed herein can be administered to a patient in need of treatment for colorectal cancer receiving a combination of chemotherapeutic agents. Exemplary combinations of chemotherapeutic agents include 5-fluorouracil (5FU) in combination with leucovorin (folinic acid or LV); capecitabine, in combination with uracil (UFT) and leucovorin; tegafur in combination with uracil (UFT) and leucovorin; oxaliplatin in combination with 5FU, or in combination with capecitabine; irinotecan in combination with capecitabine, mitomycin C in combination with 5FU, irinotecan or capecitabine. Use of other combinations of chemotherapeutic agents disclosed herein is also possible.

As is known in the relevant art, chemotherapy regimens for colorectal cancer using combinations of different chemotherapeutic agents have been standardized in clinical trials. Such regimens are often known by acronyms and include 5FU Mayo, 5FU Roswell Park, LVFU2, FOLFOX, FOLFOX4, FOLFOX6, bFOL, FUFOX, FOLFIRI, IFL, XELOX, CAPDX, XELIRI, CAPIRI, FOLFOXIRI. See, e.g., Chau, I., et al., 2009, Br. J. Cancer 100:1704-19 and Field, K., et al., 2007, World J. Gastroenterol. 13:3806-15, both of which are incorporated by reference.

Anti-hPG antibody/immune checkpoint inhibitor combinations can also be combined with other therapeutic antibodies. Accordingly, anti-hPG antibody/immune checkpoint inhibitor combination therapy can be combined with, or administered adjunctive to a different monoclonal antibody such as, for example, but not by way of limitation, an anti-EGFR (EGF receptor) monoclonal antibody or an anti-VEGF monoclonal antibody. Specific examples of anti-EGFR antibodies include cetuximab and panitumumab. A specific example of an anti-VEGF antibody is bevacizumab.

According to this embodiment, the invention relates to the anti-hPG antibody/immune checkpoint inhibitor combination described above, for the treatment of CRC, wherein said combination is administered with a chemotherapeutic agent. The anti-hPG antibody/immune checkpoint inhibitor combination and the chemotherapeutic agent can be administered simultaneously, successively, or separately.

Unless defined otherwise, all technical and scientific terms used herein have the same meaning as is commonly understood by one of the skill in the art to which this invention belongs.

FIGURE LEGENDS

FIG. 1: BALB/cAnNRj mice were implanted with a colorectal carcinoma cell line, CT26.WT, and treated with either a control antibody, an anti-PD-1 antibody, an anti-PG antibody, or a combination of an anti-PD-1 antibody and an anti-PG antibody: (A) Kaplan-Meier survival plot; (B) median survival time (in days).

Figure 2:
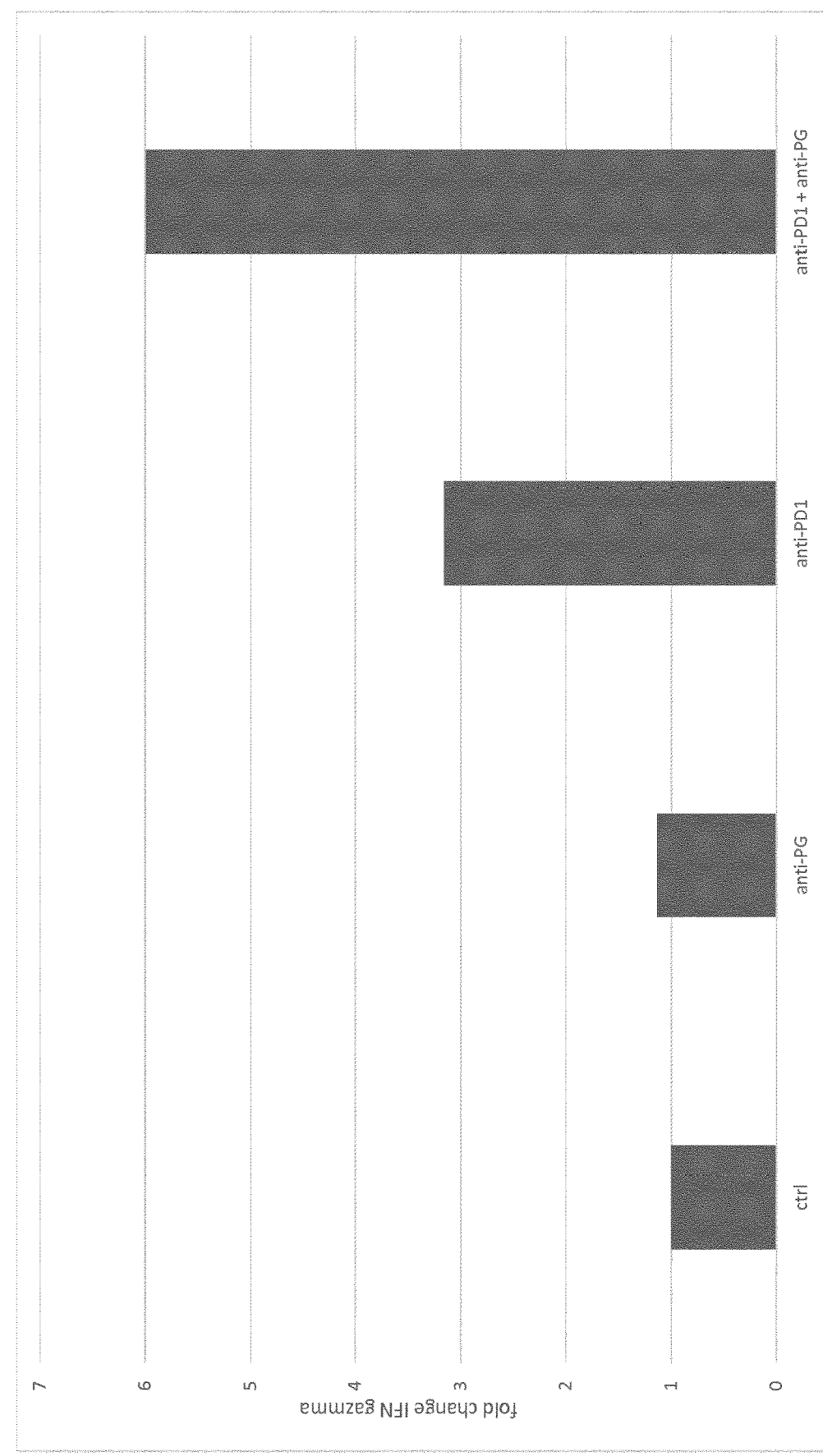

FIG. 2: qPCR analysis of INFγ expression in BALB/cAnNRj mice xenografted with a colorectal carcinoma cell line, CT26.WT, and treated with either a control antibody, an anti-PD-1 antibody, an anti-PG antibody, or a combination of an anti-PD-1 antibody and an anti-PG antibody.

EXAMPLES

Example 1

BALB/cAnNRj mice were implanted into the flank subcutaneously with 0.5 M of CT26.WT (ATCC-CRL-2638) cells per mouse on day 1. Mice were randomised into individual treatment groups (n=15 mice per group) as indicated:

Groupe ctrl: 15 mice injected with NaCl (5 mL/kg)+rat IgG2A (10 mg/kg–5 mL/kg) intraperitoneally, twice a week.

Groupe anti-PG: 15 mice injected with NaCl (5 mL/kg)+anti-PG (30 mg/kg–5 mL/kg) intraperitoneally, twice a week.

Groupe anti-PD-1: 15 mice injected with NaCl (5 mL/kg), +anti-PD1 (10 mg/kg–5 mL/kg) intraperitoneally, twice a week.

Groupe 4 anti-PG+anti-PD1: 15 mice injected with anti-PG (30 mg/kg–5 mL/kg)+anti-PD1 (10 mg/kg–5 mL/kg) intraperitoneally, twice a week.

The anti-PG antibody is Mab8, whose CDRs, $V_H$, and $V_L$ are described in Table 5.

The anti-PD-1 antibody is the 29F.1A12 monoclonal antibody (obtained from BioXCell, 10 Technology Dr, Suite 2B West Lebanon, N.H. 03784, USA)

Animals were observed and weighed twice weekly, at the same time as tumour volumes were measured using a digital caliper. Tumour size was calculated using the following formula: V=length×width$^2$/2, where length represents the largest tumour diameter and width represents the perpendicular tumour diameter. Animals were sacrificed either at the end of the study, or when tumours reached a volume of 1500 mm$^3$, if tumour ulceration was observed, if body weight loss exceeded 20% or if significant deteriorations were observed in mouse health. Euthanasia by cervical dislocation was done after gaseous anaesthesia (isoflurane).

FIG. 1 shows the Kaplan-Meier survival for each group. Log-rank (Mantel-Cox) test shows a statistical increase of the survival between the combination group (anti-PG+anti-PD1) and the single treatment (anti-PG or anti-PD1) with an increase of the median survival from 15 to 20 days (+33%, p<0.0001), confirming the superior activity of the combination compared to each of the monotherapies.

Example 2

BALB/cAnNRj mice were implanted into the flank subcutaneously with 0.5 M of CT26.WT (ATCC-CRL-2638) cells per mouse on day 1. Mice were randomized into individual treatment groups (n=15 mice per group) as indicated:

Groupe ctrl: 15 mice injected with NaCl (5 mL/kg)+rat IgG2A (10 mg/kg–5 mL/kg) intraperitoneally, twice a week.

Groupe anti-PG: 15 mice injected with NaCl (5 mL/kg)+anti-PG (30 mg/kg–5 mL/kg) intraperitoneally, twice a week.

Groupe anti-PD-1: 15 mice injected with NaCl (5 mL/kg), +anti-PD1 (10 mg/kg–5 mL/kg) intraperitoneally, twice a week.

Groupe 4 anti-PG+anti-PD1: 15 mice injected with anti-PG (30 mg/kg–5 mL/kg)+anti-PD1 (10 mg/kg–5 mL/kg) intraperitoneally, twice a week.

One week after the start of the treatment, 4 mice per group were sacrificed and the tumour were recovered to extract RNA and perform qPCR to measure the expression of interferon gamma (INFγ). Indeed, several publications have demonstrated that CTLA-4 and PD-1 inhibitors as well as other immune checkpoint blockade therapies result in an increase in IFNγ production. FIG. 2 shows that the anti-PD1 antibody induces IFNγ production in the present murine model, as expected (fold increase of 3.2). More interestingly, a greater increase of IFNγ production was observed with the combination therapy anti-PG+anti-PD1 antibodies (fold increase of 6), confirming the superior activity of the combination compared to each the monotherapies.

The invention claimed is:

1. A combination comprising:
   an anti-progastrin (anti-hPG) monoclonal antibody comprising:
      a heavy chain of amino acid sequence SEQ ID NO:49 and
      a light chain of amino acid sequence SEQ ID NO:50 and
   an immune checkpoint inhibitor, wherein said immune checkpoint inhibitor is an anti-PD1 antibody.

2. A combination comprising:
   an anti-progastrin (anti-hPG) monoclonal antibody comprising:
      a heavy chain of amino acid sequence SEQ ID NO:73 and
      a light chain of amino acid sequence SEQ ID NO:74 and
   an immune checkpoint inhibitor, wherein said immune checkpoint inhibitor is an anti-PD1 antibody.

3. The combination of claim 1, wherein said anti-hPG antibody is selected from the group consisting of single chain antibodies, camelised antibodies, chimeric antibodies, IgA1 antibodies, IgA2 antibodies, IgD antibodies, IgE antibodies, IgG1 antibodies, IgG2 antibodies, IgG3 antibodies, IgG4 antibodies, and IgM antibodies.

4. The combination of claim 1, wherein said anti-hPG antibody is a humanised antibody.

5. The combination of claim 1, wherein said anti-hPG antibody is a C-terminal anti-progastrin antibody.

6. The combination of claim 1, wherein said anti-hPG antibody is a neutralising antibody.

7. The combination of claim 1, wherein said anti-PD1 antibody is pembrolizumab, nivolumab, cemiplimab, or pidilizumab.

8. A method for treating colorectal cancer, comprising administering the combination of claim 1, to a patient in need thereof.

9. The method of claim 8, wherein said anti-hPG antibody and said immune checkpoint inhibitor are administered simultaneously, separately, or sequentially.

10. A pharmaceutical composition comprising the combination of claim 1, a pharmaceutical acceptable vehicle, and/or an excipient.

11. The combination of claim 2, wherein said anti-hPG antibody is selected from the group consisting of single chain antibodies, camelised antibodies, chimeric antibodies, IgA1 antibodies, IgA2 antibodies, IgD antibodies, IgE antibodies, IgG1 antibodies, IgG2 antibodies, IgG3 antibodies, IgG4 antibodies, and IgM antibodies.

12. The combination of claim 2, wherein said anti-hPG antibody is a humanised antibody.

13. The combination of claim 2, wherein said anti-hPG antibody is a C-terminal anti-progastrin antibody.

14. The combination of claim 2, wherein said anti-hPG antibody is a neutralising antibody.

15. The combination of claim 2, wherein said anti-PD1 antibody is pembrolizumab, nivolumab, cemiplimab, or pidilizumab.

16. A method for treating colorectal cancer, comprising administering the combination of claim 2, to a patient in need thereof.

17. The method of claim 16, wherein said anti-hPG antibody and said immune checkpoint inhibitor are administered simultaneously, separately, or sequentially.

18. A pharmaceutical composition comprising the combination of claim 2, a pharmaceutical acceptable vehicle, and/or an excipient.

\* \* \* \* \*

```
                          SEQUENCE LISTING

<160> NUMBER OF SEQ ID NOS: 78

<210> SEQ ID NO 1
<211> LENGTH: 80
<212> TYPE: PRT
<213> ORGANISM: Homo sapiens

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 2
<211> LENGTH: 14
<212> TYPE: PRT
<213> ORGANISM: Artificial
<220> FEATURE:
<223> OTHER INFORMATION: Amino acids 1-14 N-terminal extremity of human
      progastrin

<400> SEQUENCE: 2

Ser Trp Lys Pro Arg Ser Gln Gln Pro Asp Ala Pro Leu Gly
1               5                   10

<210> SEQ ID NO 3
<211> LENGTH: 26
<212> TYPE: PRT
<213> ORGANISM: Artificial
<220> FEATURE:
<223> OTHER INFORMATION: Amino acids 55-80 C-terminal extremity of human
      progastrin

<400> SEQUENCE: 3

Gln Gly Pro Trp Leu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 4
<211> LENGTH: 8
<212> TYPE: PRT
<213> ORGANISM: Artificial
<220> FEATURE:
<223> OTHER INFORMATION: synthetic peptide

<400> SEQUENCE: 4

Gly Tyr Ile Phe Thr Ser Tyr Trp
1               5

<210> SEQ ID NO 5
<211> LENGTH: 8
```

```
<212> TYPE: PRT
<213> ORGANISM: Artificial
<220> FEATURE:
<223> OTHER INFORMATION: synthetic peptide

<400> SEQUENCE: 5

Phe Tyr Pro Gly Asn Ser Asp Ser
1               5

<210> SEQ ID NO 6
<211> LENGTH: 8
<212> TYPE: PRT
<213> ORGANISM: Artificial
<220> FEATURE:
<223> OTHER INFORMATION: synthetic peptide

<400> SEQUENCE: 6

Thr Arg Arg Asp Ser Pro Gln Tyr
1               5

<210> SEQ ID NO 7
<211> LENGTH: 11
<212> TYPE: PRT
<213> ORGANISM: Artificial
<220> FEATURE:
<223> OTHER INFORMATION: synthetic peptide

<400> SEQUENCE: 7

Gln Ser Ile Val His Ser Asn Gly Asn Thr Tyr
1               5                   10

<210> SEQ ID NO 8
<211> LENGTH: 3
<212> TYPE: PRT
<213> ORGANISM: Artificial
<220> FEATURE:
<223> OTHER INFORMATION: synthetic peptide

<400> SEQUENCE: 8

Lys Val Ser
1

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Phe Gln Gly Ser His Val Pro Phe Thr
1               5

<210> SEQ ID NO 10
<211> LENGTH: 7
<212> TYPE: PRT
<213> ORGANISM: Artificial
<220> FEATURE:
<223> OTHER INFORMATION: synthetic peptide

<400> SEQUENCE: 10

Gly Tyr Thr Phe Ser Ser Trp
1               5

<210> SEQ ID NO 11
<211> LENGTH: 8
<212> TYPE: PRT
```

```
<213> ORGANISM: Artificial
<220> FEATURE:
<223> OTHER INFORMATION: synthetic peptide

<400> SEQUENCE: 11

Phe Leu Pro Gly Ser Gly Ser Thr
1               5

<210> SEQ ID NO 12
<211> LENGTH: 11
<212> TYPE: PRT
<213> ORGANISM: Artificial
<220> FEATURE:
<223> OTHER INFORMATION: synthetic peptide

<400> SEQUENCE: 12

Ala Thr Asp Gly Asn Tyr Asp Trp Phe Ala Tyr
1               5                   10

<210> SEQ ID NO 13
<211> LENGTH: 11
<212> TYPE: PRT
<213> ORGANISM: Artificial
<220> FEATURE:
<223> OTHER INFORMATION: synthetic peptide

<400> SEQUENCE: 13

Gln Ser Leu Val His Ser Ser Gly Val Thr Tyr
1               5                   10

<210> SEQ ID NO 14
<211> LENGTH: 3
<212> TYPE: PRT
<213> ORGANISM: Artificial
<220> FEATURE:
<223> OTHER INFORMATION: synthetic peptide

<400> SEQUENCE: 14

Lys Val Ser
1

<210> SEQ ID NO 15
<211> LENGTH: 9
<212> TYPE: PRT
<213> ORGANISM: Artificial
<220> FEATURE:
<223> OTHER INFORMATION: synthetic peptide

<400> SEQUENCE: 15

Ser Gln Ser Thr His Val Pro Pro Thr
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16

Gly Tyr Thr Phe Thr Ser Tyr Tyr
1               5

<210> SEQ ID NO 17
<211> LENGTH: 8
<212> TYPE: PRT
<213> ORGANISM: Artificial
```

```
<220> FEATURE:
<223> OTHER INFORMATION: synthetic peptide

<400> SEQUENCE: 17

Ile Asn Pro Ser Asn Gly Gly Thr
1               5

<210> SEQ ID NO 18
<211> LENGTH: 10
<212> TYPE: PRT
<213> ORGANISM: Artificial
<220> FEATURE:
<223> OTHER INFORMATION: synthetic peptide

<400> SEQUENCE: 18

Thr Arg Gly Gly Tyr Tyr Pro Phe Asp Tyr
1               5                   10

<210> SEQ ID NO 19
<211> LENGTH: 11
<212> TYPE: PRT
<213> ORGANISM: Artificial
<220> FEATURE:
<223> OTHER INFORMATION: synthetic peptide

<400> SEQUENCE: 19

Gln Ser Leu Leu Asp Ser Asp Gly Lys Thr Tyr
1               5                   10

<210> SEQ ID NO 20
<211> LENGTH: 3
<212> TYPE: PRT
<213> ORGANISM: Artificial
<220> FEATURE:
<223> OTHER INFORMATION: synthetic peptide

<400> SEQUENCE: 20

Leu Val Ser
1

<210> SEQ ID NO 21
<211> LENGTH: 9
<212> TYPE: PRT
<213> ORGANISM: Artificial
<220> FEATURE:
<223> OTHER INFORMATION: synthetic peptide

<400> SEQUENCE: 21

Trp Gln Gly Thr His Ser Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: synthetic peptide

<400> SEQUENCE: 22

Gly Tyr Ser Ile Thr Ser Asp Tyr Ala
1               5

<210> SEQ ID NO 23
<211> LENGTH: 7
<212> TYPE: PRT
<213> ORGANISM: Artificial
<220> FEATURE:
```

```
<223> OTHER INFORMATION: synthetic peptide

<400> SEQUENCE: 23

Ile Ser Phe Ser Gly Tyr Thr
1               5

<210> SEQ ID NO 24
<211> LENGTH: 14
<212> TYPE: PRT
<213> ORGANISM: Artificial
<220> FEATURE:
<223> OTHER INFORMATION: synthetic peptide

<400> SEQUENCE: 24

Ala Arg Glu Val Asn Tyr Gly Asp Ser Tyr His Phe Asp Tyr
1               5                   10

<210> SEQ ID NO 25
<211> LENGTH: 7
<212> TYPE: PRT
<213> ORGANISM: Artificial
<220> FEATURE:
<223> OTHER INFORMATION: synthetic peptide

<400> SEQUENCE: 25

Ser Gln His Arg Thr Tyr Thr
1               5

<210> SEQ ID NO 26
<211> LENGTH: 7
<212> TYPE: PRT
<213> ORGANISM: Artificial
<220> FEATURE:
<223> OTHER INFORMATION: synthetic peptide

<400> SEQUENCE: 26

Val Lys Lys Asp Gly Ser His
1               5

<210> SEQ ID NO 27
<211> LENGTH: 13
<212> TYPE: PRT
<213> ORGANISM: Artificial
<220> FEATURE:
<223> OTHER INFORMATION: synthetic peptide

<400> SEQUENCE: 27

Gly Val Gly Asp Ala Ile Lys Gly Gln Ser Val Phe Val
1               5                   10

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Gly Phe Thr Phe Thr Thr Tyr Ala
1               5

<210> SEQ ID NO 29
<211> LENGTH: 8
<212> TYPE: PRT
<213> ORGANISM: Artificial
<220> FEATURE:
<223> OTHER INFORMATION: synthetic peptide
```

```
<400> SEQUENCE: 29

Ile Ser Ser Gly Gly Thr Tyr Thr
1               5

<210> SEQ ID NO 30
<211> LENGTH: 10
<212> TYPE: PRT
<213> ORGANISM: Artificial
<220> FEATURE:
<223> OTHER INFORMATION: synthetic peptide

<400> SEQUENCE: 30

Ala Thr Gln Gly Asn Tyr Ser Leu Asp Phe
1               5                   10

<210> SEQ ID NO 31
<211> LENGTH: 11
<212> TYPE: PRT
<213> ORGANISM: Artificial
<220> FEATURE:
<223> OTHER INFORMATION: synthetic peptide

<400> SEQUENCE: 31

Lys Ser Leu Arg His Thr Lys Gly Ile Thr Phe
1               5                   10

<210> SEQ ID NO 32
<211> LENGTH: 3
<212> TYPE: PRT
<213> ORGANISM: Artificial
<220> FEATURE:
<223> OTHER INFORMATION: synthetic peptide

<400> SEQUENCE: 32

Gln Met Ser
1

<210> SEQ ID NO 33
<211> LENGTH: 9
<212> TYPE: PRT
<213> ORGANISM: Artificial
<220> FEATURE:
<223> OTHER INFORMATION: synthetic peptide

<400> SEQUENCE: 33

Ala Gln Asn Leu Glu Leu Pro Leu Thr
1               5

<210> SEQ ID NO 34
<211> LENGTH: 8
<212> TYPE: PRT
<213> ORGANISM: Artificial
<220> FEATURE:
<223> OTHER INFORMATION: synthetic peptide

<400> SEQUENCE: 34

Gly Phe Ile Phe Ser Ser Tyr Gly
1               5

<210> SEQ ID NO 35
<211> LENGTH: 8
<212> TYPE: PRT
<213> ORGANISM: Artificial
<220> FEATURE:
<223> OTHER INFORMATION: synthetic peptide
```

```
<400> SEQUENCE: 35

Ile Asn Thr Phe Gly Asp Arg Thr
1               5

<210> SEQ ID NO 36
<211> LENGTH: 7
<212> TYPE: PRT
<213> ORGANISM: Artificial
<220> FEATURE:
<223> OTHER INFORMATION: synthetic peptide

<400> SEQUENCE: 36

Ala Arg Gly Thr Gly Thr Tyr
1               5

<210> SEQ ID NO 37
<211> LENGTH: 11
<212> TYPE: PRT
<213> ORGANISM: Artificial
<220> FEATURE:
<223> OTHER INFORMATION: synthetic peptide

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial
<220> FEATURE:
<223> OTHER INFORMATION: synthetic peptide

<400> SEQUENCE: 38

Leu Val Ser
1

<210> SEQ ID NO 39
<211> LENGTH: 9
<212> TYPE: PRT
<213> ORGANISM: Artificial
<220> FEATURE:
<223> OTHER INFORMATION: synthetic peptide

<400> SEQUENCE: 39

Trp Gln Gly Thr His Phe Pro Gln Thr
1               5

<210> SEQ ID NO 40
<211> LENGTH: 10
<212> TYPE: PRT
<213> ORGANISM: Artificial
<220> FEATURE:
<223> OTHER INFORMATION: Amino acids 71-80 C-terminal extremity of human
      progastrin

<400> SEQUENCE: 40

Phe Gly Arg Arg Ser Ala Glu Asp Glu Asn
1               5                   10

<210> SEQ ID NO 41
<211> LENGTH: 115
<212> TYPE: PRT
<213> ORGANISM: Artificial
<220> FEATURE:
<223> OTHER INFORMATION: synthetic peptide
```

```
<400> SEQUENCE: 41

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 42
<211> LENGTH: 112
<212> TYPE: PRT
<213> ORGANISM: Artificial
<220> FEATURE:
<223> OTHER INFORMATION: synthetic peptide

<400> SEQUENCE: 42

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 43
<211> LENGTH: 118
<212> TYPE: PRT
<213> ORGANISM: Artificial
<220> FEATURE:
<223> OTHER INFORMATION: synthetic peptide

<400> SEQUENCE: 43

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
    50                  55                  60
```

```
Lys Gly Lys Ala Thr Phe Thr Ala Asp Thr Ser Ser Asp Thr Ala Tyr
 65                  70                  75                  80

Met Leu Leu Ser Ser Leu Thr Ser Glu Asp Ser Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 44
<211> LENGTH: 112
<212> TYPE: PRT
<213> ORGANISM: Artificial
<220> FEATURE:
<223> OTHER INFORMATION: synthetic peptide

<400> SEQUENCE: 44

Asp Leu Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Ser Gly Val Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Ser Gly Thr Lys Leu Glu Ile Lys
            100                 105                 110

<210> SEQ ID NO 45
<211> LENGTH: 117
<212> TYPE: PRT
<213> ORGANISM: Artificial
<220> FEATURE:
<223> OTHER INFORMATION: synthetic peptide

<400> SEQUENCE: 45

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Tyr Met Tyr Trp Val Lys Gln Arg Pro Gly Gln Gly Leu Glu Trp Ile
         35                  40                  45

Gly Glu Ile Asn Pro Ser Gly Gly Thr Asn Phe Asn Glu Lys Phe
     50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Gly Tyr Tyr Pro Phe Asp Tyr Trp Gly Gln Gly Thr Thr
            100                 105                 110

Leu Thr Val Ser Ser
        115

<210> SEQ ID NO 46
```

<211> LENGTH: 112
<212> TYPE: PRT
<213> ORGANISM: Artificial
<220> FEATURE:
<223> OTHER INFORMATION: synthetic peptide

<400> SEQUENCE: 46

Asp Val Val Met Thr Gln Thr Pro Leu Thr Leu Ser Val Thr Ile Gly
1               5                   10                  15

Arg Pro Ala Ser Ile Ser Cys Lys Ser Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 47
<211> LENGTH: 121
<212> TYPE: PRT
<213> ORGANISM: Artificial
<220> FEATURE:
<223> OTHER INFORMATION: synthetic peptide

<400> SEQUENCE: 47

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 48
<211> LENGTH: 115
<212> TYPE: PRT
<213> ORGANISM: Artificial
<220> FEATURE:
<223> OTHER INFORMATION: synthetic peptide

<400> SEQUENCE: 48

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30

```
Ile Glu Trp Tyr Gln Gln Gln Ser Leu Lys Pro Pro Lys Tyr Val Met
         35                  40                  45

Glu Val Lys Lys Asp Gly Ser His Ser Thr Gly His Gly Ile Pro Asp
 50                  55                  60

Arg Phe Ser Gly Ser Ser Gly Ala Asp Arg Tyr Leu Ser Ile Ser
 65                  70                  75                  80

Asn Ile Gln Pro Glu Asp Glu Ala Ile Tyr Ile Cys Gly Val Gly Asp
                 85                  90                  95

Ala Ile Lys Gly Gln Ser Val Phe Val Phe Gly Gly Thr Lys Val
                100                 105                 110

Thr Val Leu
        115

<210> SEQ ID NO 49
<211> LENGTH: 117
<212> TYPE: PRT
<213> ORGANISM: Artificial
<220> FEATURE:
<223> OTHER INFORMATION: synthetic peptide

<400> SEQUENCE: 49

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Thr Tyr
                 20                  25                  30

Ala Met Ser Trp Val Arg Gln Ala Pro Gly Lys Gly Leu Glu Trp Val
         35                  40                  45

Ala Thr Ile Ser Ser Gly Gly Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Thr Gln Gly Asn Tyr Ser Leu Asp Phe Trp Gly Gln Gly Thr Thr
                100                 105                 110

Val Thr Val Ser Ser
        115

<210> SEQ ID NO 50
<211> LENGTH: 112
<212> TYPE: PRT
<213> ORGANISM: Artificial
<220> FEATURE:
<223> OTHER INFORMATION: synthetic peptide

<400> SEQUENCE: 50

Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Arg His Thr
                 20                  25                  30

Lys Gly Ile Thr Phe Leu Tyr Trp Tyr Leu Gln Lys Pro Gly Gln Ser
         35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95
```

Leu Glu Leu Pro Leu Thr Phe Gly Gly Gly Thr Lys Val Glu Ile Lys
            100                 105                 110

<210> SEQ ID NO 51
<211> LENGTH: 114
<212> TYPE: PRT
<213> ORGANISM: Artificial
<220> FEATURE:
<223> OTHER INFORMATION: synthetic peptide

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Ser Glu Asp Thr Ala Ile Tyr Tyr Cys
                85                  90                  95

Ala Arg Gly Thr Gly Thr Tyr Trp Gly Gln Gly Thr Leu Thr Val
            100                 105                 110

Ser Ser

<210> SEQ ID NO 52
<211> LENGTH: 112
<212> TYPE: PRT
<213> ORGANISM: Artificial
<220> FEATURE:
<223> OTHER INFORMATION: synthetic peptide

<400> SEQUENCE: 52

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 53
<211> LENGTH: 115
<212> TYPE: PRT
<213> ORGANISM: Artificial
<220> FEATURE:
<223> OTHER INFORMATION: synthetic peptide

<400> SEQUENCE: 53

Gln Val Gln Leu Val Gln Ser Gly Ala Glu Val Lys Lys Pro Gly Ala

```
            1               5                  10                 15
Ser Val Lys Val Ser Cys Lys Ala Ser Gly Tyr Ile Phe Thr Ser Tyr
                20                  25                 30

Trp Val His Trp Val Arg Gln Ala Pro Gly Gln Arg Leu Glu Trp Met
            35                  40                 45

Gly Gly Phe Tyr Pro Gly Asn Ser Asp Ser Arg Tyr Ser Gln Lys Phe
        50                  55                 60

Gln Gly Arg Val Thr Ile Thr Arg Asp Thr Ser Ala Ser Thr Ala Tyr
65                  70                  75                 80

Met Glu Leu Ser Ser Leu Arg Ser Glu Asp Thr Ala Val Tyr Tyr Cys
                85                  90                 95

Thr Arg Arg Asp Ser Pro Gln Tyr Trp Gly Gln Gly Thr Leu Val Thr
                100                 105                110

Val Ser Ser
        115
```

<210> SEQ ID NO 54
<211> LENGTH: 112
<212> TYPE: PRT
<213> ORGANISM: Artificial
<220> FEATURE:
<223> OTHER INFORMATION: synthetic peptide

<400> SEQUENCE: 54

```
Asp Val Val Met Thr Gln Ser Pro Leu Ser Leu Pro Val Thr Leu Gly
1               5                   10                 15

Gln Pro Ala Ser Ile Ser Cys Arg Ser Ser Gln Ser Ile Val His Ser
                20                  25                 30

Asn Gly Asn Thr Tyr Leu Glu Trp Phe Gln Gln Arg Pro Gly Gln Ser
            35                  40                 45

Pro Arg Arg Leu Ile Tyr Lys Val Ser Asn Arg Phe Ser Gly Val Pro
        50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Phe Gln Gly
                85                  90                 95

Ser His Val Pro Phe Thr Phe Gly Gly Gly Thr Lys Val Glu Ile Lys
                100                 105                110
```

<210> SEQ ID NO 55
<211> LENGTH: 118
<212> TYPE: PRT
<213> ORGANISM: Artificial
<220> FEATURE:
<223> OTHER INFORMATION: synthetic peptide

<400> SEQUENCE: 55

```
Gln Val Gln Leu Val Gln Ser Gly Ala Glu Val Lys Lys Pro Gly Ala
1               5                   10                 15

Ser Val Lys Val Ser Cys Lys Ala Ser Gly Tyr Thr Phe Ser Ser Ser
                20                  25                 30

Trp Met His Trp Val Arg Gln Ala Pro Gly Gln Gly Leu Glu Trp Met
            35                  40                 45

Gly Ile Phe Leu Pro Gly Ser Gly Ser Thr Asp Tyr Ala Gln Lys Phe
        50                  55                 60

Gln Gly Arg Val Thr Met Thr Arg Asp Thr Ser Thr Ser Thr Val Tyr
65                  70                  75                 80
```

```
Met Glu Leu Ser Ser Leu Arg Ser Glu Asp Thr Ala Val Tyr Tyr Cys
                85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 56
<211> LENGTH: 112
<212> TYPE: PRT
<213> ORGANISM: Artificial
<220> FEATURE:
<223> OTHER INFORMATION: synthetic peptide

<400> SEQUENCE: 56

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 57
<211> LENGTH: 117
<212> TYPE: PRT
<213> ORGANISM: Artificial
<220> FEATURE:
<223> OTHER INFORMATION: synthetic peptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 58
<211> LENGTH: 117
<212> TYPE: PRT
<213> ORGANISM: Artificial
```

```
<220> FEATURE:
<223> OTHER INFORMATION: synthetic peptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 59
<211> LENGTH: 117
<212> TYPE: PRT
<213> ORGANISM: Artificial
<220> FEATURE:
<223> OTHER INFORMATION: synthetic peptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115

<210> SEQ ID NO 60
<211> LENGTH: 112
<212> TYPE: PRT
<213> ORGANISM: Artificial
<220> FEATURE:
<223> OTHER INFORMATION: synthetic peptide

<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30
```

Asp Gly Lys Thr Tyr Leu Tyr Trp Phe Gln Gln Arg Pro Gly Gln Ser
                35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
                100                 105                 110

<210> SEQ ID NO 61
<211> LENGTH: 112
<212> TYPE: PRT
<213> ORGANISM: Artificial
<220> FEATURE:
<223> OTHER INFORMATION: synthetic peptide

<400> SEQUENCE: 61

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
                20                  25                  30

Asp Gly Lys Thr Tyr Leu Asn Trp Phe Gln Gln Arg Pro Gly Gln Ser
                35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
                100                 105                 110

<210> SEQ ID NO 62
<211> LENGTH: 112
<212> TYPE: PRT
<213> ORGANISM: Artificial
<220> FEATURE:
<223> OTHER INFORMATION: synthetic peptide

<400> SEQUENCE: 62

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
                20                  25                  30

Asp Gly Lys Thr Tyr Leu Tyr Trp Phe Gln Gln Arg Pro Gly Gln Ser
                35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
                100                 105                 110

<210> SEQ ID NO 63

<211> LENGTH: 121
<212> TYPE: PRT
<213> ORGANISM: Artificial
<220> FEATURE:
<223> OTHER INFORMATION: synthetic peptide

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial
<220> FEATURE:
<223> OTHER INFORMATION: synthetic peptide

<400> SEQUENCE: 64

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial
<220> FEATURE:
<223> OTHER INFORMATION: synthetic peptide

<400> SEQUENCE: 65

Gln Val Gln Leu Gln Glu Ser Gly Pro Gly Leu Val Lys Pro Ser Gln
1               5                   10                  15

```
Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
            115                 120
```

<210> SEQ ID NO 66
<211> LENGTH: 115
<212> TYPE: PRT
<213> ORGANISM: Artificial
<220> FEATURE:
<223> OTHER INFORMATION: synthetic peptide

<400> SEQUENCE: 66

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115
```

<210> SEQ ID NO 67
<211> LENGTH: 115
<212> TYPE: PRT
<213> ORGANISM: Artificial
<220> FEATURE:
<223> OTHER INFORMATION: synthetic peptide

<400> SEQUENCE: 67

```
Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Ala Trp His Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80
```

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
                100                 105                 110

Glu Ile Lys
        115

<210> SEQ ID NO 68
<211> LENGTH: 115
<212> TYPE: PRT
<213> ORGANISM: Artificial
<220> FEATURE:
<223> OTHER INFORMATION: synthetic peptide

<400> SEQUENCE: 68

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
            35                  40                  45

Glu Val Lys Lys Asp Gly Ser His Ser Lys Gly Asp Gly Ile Pro Asp
        50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
                100                 105                 110

Glu Ile Lys
        115

<210> SEQ ID NO 69
<211> LENGTH: 117
<212> TYPE: PRT
<213> ORGANISM: Artificial
<220> FEATURE:
<223> OTHER INFORMATION: synthetic peptide

<400> SEQUENCE: 69

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
                20                  25                  30

Ala Met Ser Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

<210> SEQ ID NO 70
<211> LENGTH: 112
<212> TYPE: PRT
<213> ORGANISM: Artificial
<220> FEATURE:
<223> OTHER INFORMATION: synthetic peptide

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 71
<211> LENGTH: 117
<212> TYPE: PRT
<213> ORGANISM: Artificial
<220> FEATURE:
<223> OTHER INFORMATION: synthetic peptide

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 72
<211> LENGTH: 112
<212> TYPE: PRT
<213> ORGANISM: Artificial
<220> FEATURE:
<223> OTHER INFORMATION: synthetic peptide

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
                35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Lys Ile
 65                  70                  75                  80

Ser Arg Val Glu Ala Glu Asp Val Gly Val Tyr Tyr Cys Ala Gln Asn
                 85                  90                  95

Leu Glu Leu Pro Leu Thr Phe Gly Gly Gly Thr Lys Val Glu Ile Lys
                100                 105                 110

<210> SEQ ID NO 73
<211> LENGTH: 447
<212> TYPE: PRT
<213> ORGANISM: Artificial
<220> FEATURE:
<223> OTHER INFORMATION: synthetic peptide

<400> SEQUENCE: 73

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Thr Tyr
                20                  25                  30

Ala Met Ser Trp Val Arg Gln Ala Pro Gly Lys Gly Leu Glu Trp Val
                35                  40                  45

Ala Thr Ile Ser Ser Gly Gly Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
 130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
 210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 74
<211> LENGTH: 219
<212> TYPE: PRT
<213> ORGANISM: Artificial
<220> FEATURE:
<223> OTHER INFORMATION: synthetic peptide

<400> SEQUENCE: 74

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 75
<211> LENGTH: 114
<212> TYPE: PRT
<213> ORGANISM: Artificial
<220> FEATURE:
<223> OTHER INFORMATION: synthetic peptide

<400> SEQUENCE: 75

Glu Val Gln Leu Val Glu Ser Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial
<220> FEATURE:
<223> OTHER INFORMATION: synthetic peptide

<400> SEQUENCE: 76

Glu Val Gln Leu Val Glu Ser Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 77
<211> LENGTH: 112
<212> TYPE: PRT
<213> ORGANISM: Artificial
<220> FEATURE:
<223> OTHER INFORMATION: synthetic peptide

<400> SEQUENCE: 77

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 78
<211> LENGTH: 112
<212> TYPE: PRT
<213> ORGANISM: Artificial
<220> FEATURE:
<223> OTHER INFORMATION: synthetic peptide

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110
```